US008586712B2

(12) United States Patent
Fang et al.

(10) Patent No.: US 8,586,712 B2
(45) Date of Patent: *Nov. 19, 2013

(54) HUMANIZED ANTIBODIES

(75) Inventors: Fang Fang, San Diego, CA (US); Lori Kohlstaedt, La Jolla, CA (US); John Reno, San Diego, CA (US)

(73) Assignee: Perlan Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,304

(22) Filed: Mar. 26, 2010

(65) Prior Publication Data

US 2011/0044976 A1    Feb. 24, 2011

Related U.S. Application Data

(60) Division of application No. 11/519,322, filed on Sep. 11, 2006, now Pat. No. 7,696,324, which is a continuation of application No. 09/910,483, filed on Jul. 19, 2001, now abandoned, which is a continuation-in-part of application No. 09/555,446, filed as application No. PCT/US98/25422 on Nov. 30, 1998, now abandoned.

(51) Int. Cl.
C07K 16/28        (2006.01)
C12N 15/13        (2006.01)
C12N 15/63        (2006.01)
A61K 39/395       (2006.01)

(52) U.S. Cl.
USPC ............. 530/387.3; 536/23.53; 435/320.1; 424/133.1

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 4,698,420 A | 10/1987 | Urnovitz |
| 4,844,904 A | 7/1989 | Hamaguchi et al. |
| 4,863,740 A | 9/1989 | Kissel et al. |
| 4,946,778 A | 8/1990 | Ladner et al. |
| 4,975,282 A | 12/1990 | Cullis et al. |
| 5,000,959 A | 3/1991 | Iga et al. |
| 5,077,195 A | 12/1991 | Blalock et al. |
| 5,081,584 A | 1/1992 | Omichinski et al. |
| 5,223,396 A | 6/1993 | Rothlein et al. |
| 5,223,409 A | 6/1993 | Ladner et al. |
| 5,225,539 A | 7/1993 | Winter |
| 5,260,203 A | 11/1993 | Ladner et al. |
| 5,324,510 A | 6/1994 | Wegner et al. |
| 5,455,030 A | 10/1995 | Ladner et al. |
| 5,459,127 A | 10/1995 | Felgner et al. |
| 5,475,091 A | 12/1995 | Springer et al. |
| 5,491,074 A | 2/1996 | Aldwin et al. |
| 5,501,979 A | 3/1996 | Geller et al. |
| 5,530,101 A | 6/1996 | Queen et al. |
| 5,561,063 A | 10/1996 | Hock et al. |
| 5,565,332 A | 10/1996 | Hoogenboom et al. |
| 5,565,550 A | 10/1996 | Springer et al. |
| 5,573,925 A | 11/1996 | Halazonetis |
| 5,582,996 A | 12/1996 | Curtis |
| 5,585,089 A | 12/1996 | Queen et al. |
| 5,604,090 A | 2/1997 | Alexander et al. |
| 5,624,820 A | 4/1997 | Cooper |
| 5,639,641 A | 6/1997 | Pedersen et al. |
| 5,665,577 A | 9/1997 | Sodroski et al. |
| 5,674,703 A | 10/1997 | Woo et al. |
| 5,693,508 A | 12/1997 | Chang |
| 5,693,761 A | 12/1997 | Queen et al. |
| 5,693,762 A | 12/1997 | Queen et al. |
| 5,700,470 A | 12/1997 | Saito et al. |
| 5,716,805 A | 2/1998 | Srinivasan et al. |
| 5,719,054 A | 2/1998 | Boursnell et al. |
| 5,721,340 A | 2/1998 | Halazonetis |
| 5,723,286 A | 3/1998 | Dower et al. |
| 5,731,168 A | 3/1998 | Carter et al. |
| 5,731,172 A | 3/1998 | Saito et al. |
| 5,763,733 A | 6/1998 | Whitlow et al. |
| 5,786,340 A | 7/1998 | Henning et al. |
| 5,807,706 A | 9/1998 | Carter et al. |
| 5,821,123 A | 10/1998 | Studnicka |
| 5,821,235 A | 10/1998 | Henning et al. |
| 5,821,333 A | 10/1998 | Carter et al. |
| 5,821,337 A | 10/1998 | Carter et al. |

(Continued)

FOREIGN PATENT DOCUMENTS

| | | |
|---|---|---|
| CA | 2407426 | 11/2001 |
| EP | 0169146 A2 | 1/1986 |

(Continued)

OTHER PUBLICATIONS

Jedrzejas et al (Acta Crystallographica D51:380-385, 1995).*
Schneider et al (European Neurology 40:78-83, 1998).*
Vuorte et al (Journal of Immunology 162:2353-2357, 1999).*
Hayden et al (Antiviral Research 9: 233-247, 1988).*
Colonno et al (Journal of Virology 57: 7-12, 1986).*
Lineburger et al (Journal of Virology 64: 2582-2587, 1990).*
Luo et al (Journal of Immunological Methods 275:31-40, 2003).*
Fang et al (Journal of Antimicrobial Chemotherapy 53:23-25, 2004).*
U.S. Appl. No. 09/555,446, filed Aug. 16, 2000, Fang et al.
U.S. Appl. No. 09/674,014, filed Feb. 8, 2001, Fang et al.
Altschul et al., Basic Local Alignment Search Tool, J. Mol. Biol. 215:403-410 (1990).

(Continued)

Primary Examiner — Mary E Mosher
(74) Attorney, Agent, or Firm — Jones Day

(57) ABSTRACT

Humanized antibodies that bind ICAM-1 are provided. Antibodies include those selected from: SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI). Subsequences of the humanized antibodies capable of binding an ICAM-1 epitope are also provided. Methods of inhibiting pathogen infection (e.g., HRV) of a cell employing humanized antibodies capable of binding an ICAM-1 epitope are further provided.

53 Claims, 6 Drawing Sheets

(56) References Cited

U.S. PATENT DOCUMENTS

| | | | |
|---|---|---|---|
| 5,837,242 A | 11/1998 | Holliger et al. | |
| 5,856,456 A | 1/1999 | Whitlow et al. | |
| 5,861,397 A | 1/1999 | Wheeler | |
| 5,869,620 A | 2/1999 | Whitlow et al. | |
| 5,910,573 A | 6/1999 | Plückthun et al. | |
| 5,928,944 A | 7/1999 | Seth et al. | |
| 5,932,448 A | 8/1999 | Tso et al. | |
| 5,942,433 A | 8/1999 | Vinson et al. | |
| 5,965,712 A | 10/1999 | Conrad et al. | |
| 6,013,516 A | 1/2000 | Verma et al. | |
| 6,025,165 A | 2/2000 | Whitlow et al. | |
| 6,027,725 A | 2/2000 | Whitlow et al. | |
| 6,071,515 A | 6/2000 | Mezes et al. | |
| 6,096,291 A | 8/2000 | Betbeder et al. | |
| 6,110,456 A | 8/2000 | During | |
| 6,121,424 A | 9/2000 | Whitlow et al. | |
| 6,129,914 A | 10/2000 | Weiner et al. | |
| 6,190,886 B1 | 2/2001 | Hoppe et al. | |
| 6,218,513 B1 | 4/2001 | Anthony-Cahill et al. | |
| 6,307,026 B1 | 10/2001 | King et al. | |
| 6,329,507 B1 | 12/2001 | Mezes et al. | |
| 6,329,511 B1 | 12/2001 | Vasquez et al. | |
| 6,800,735 B2 | 10/2004 | Whitty et al. | |
| 7,696,324 B2 * | 4/2010 | Fang et al. | 530/387.3 |
| 2002/0165153 A1 | 11/2002 | Angel et al. | |
| 2003/0035798 A1 | 2/2003 | Fang et al. | |
| 2003/0138440 A1 | 7/2003 | Fang et al. | |

FOREIGN PATENT DOCUMENTS

| | | |
|---|---|---|
| EP | 0239400 B1 | 9/1987 |
| EP | 0387701 B1 | 9/1990 |
| EP | 0404003 A2 | 12/1990 |
| EP | 0451216 B1 | 10/1991 |
| EP | 0459577 * | 12/1991 |
| EP | 0528931 B1 | 3/1993 |
| EP | 0605522 B1 | 7/1994 |
| EP | 0654085 B1 | 5/1995 |
| EP | 0365837 B1 | 8/1995 |
| EP | 0672142 B1 | 9/1995 |
| EP | 0682040 B1 | 11/1995 |
| EP | 0939127 A2 | 9/1999 |
| EP | 0967277 A2 | 12/1999 |
| EP | 1 039 931 B1 | 4/2005 |
| JP | 10-101699 | 4/1998 |
| JP | 2005100185 | 4/2005 |
| WO | WO 88/01649 | 3/1988 |
| WO | WO 90/07861 | 7/1990 |
| WO | WO 91/07418 | 5/1991 |
| WO | WO 91/07493 | 5/1991 |
| WO | WO 91/07494 | 5/1991 |
| WO | WO 91/16927 | 11/1991 |
| WO | WO 91/16928 | 11/1991 |
| WO | WO 92/05266 | 4/1992 |
| WO | WO 92/11018 | 7/1992 |
| WO | WO 92/14829 | 9/1992 |
| WO | WO 92/22653 | 12/1992 |
| WO | WO 93/06213 | 4/1993 |
| WO | WO 93/11161 | 6/1993 |
| WO | WO 93/11162 | 6/1993 |
| WO | WO 93/11794 | 6/1993 |
| WO | WO 93/15210 | 8/1993 |
| WO | WO 93/23434 | 11/1993 |
| WO | WO 94/04679 | 3/1994 |
| WO | WO 94/13804 | 6/1994 |
| WO | WO 94/18318 | 8/1994 |
| WO | WO 94/20078 | 9/1994 |
| WO | WO 95/08577 | 3/1995 |
| WO | WO 95/27736 | 10/1995 |
| WO | WO 96/13583 | 5/1996 |
| WO | WO 96/34015 | 10/1996 |
| WO | WO 96/37621 | 11/1996 |
| WO | WO 97/23631 | 7/1997 |
| WO | WO 98/50431 | 11/1998 |
| WO | WO 99/10510 | 3/1999 |
| WO | WO 99/27964 | 6/1999 |
| WO | WO 99/55911 | 11/1999 |
| WO | WO 00/09073 | 2/2000 |
| WO | WO 00/23472 | 4/2000 |
| WO | WO 01/00814 A3 | 1/2001 |
| WO | WO 01/19842 A1 | 3/2001 |
| WO | WO 03/035696 | 5/2003 |
| WO | WO 03/062370 | 7/2003 |

OTHER PUBLICATIONS

Bastiani et al., Host cell-dependent alterations in envelope components of human immunodeficiency virus type 1 virions. Journal of Virology, May 1997, pp. 3444-3450.

Behera et al., Blocking intercellular adhesion molecule-1 on human epithelial cells decreases respiratory syncytial virus infection. Biochemical and biophysical research communications 280(1):188-195, Jan. 12, 2001.

Bitter et al., Expression and Secretion Vectors for Yeast, Methods in Enzymology, Acad. Press, N.Y., 153:516-544 (1987).

Bitter, Grant A., Heterologous Gene Expression in Yeast, Methods in Enzymology, Acad. Press, N.Y., vol. 152, pp. 673-684 (1987).

Carter et al., "Humanization of an anti-p185(HER2) antibody for human cancer therapy," (1992), Proc. Natl. Acad. Sci., vol. 89, pp. 4285-4289.

Charles et al., Prevention of Human Rhinovirus Infection by Multivalent Fab Molecules Directed Against ICAM-1. Antimicrobial Agents and Chemotherapy, 2003, 1503-1508.

Chothia et al., Conformations of immunoglobulin hypervariable regions, Nature, 342:877-883 (1989).

Chothia et al., Domain Association in Immunoglobulin Molecules, The Packing of Variable Domains, J. Mol. Biol., 186:651-663 (1985).

Chothia et al., Structural Repertoire of the Human $V_H$ Segments, J. Mol. Biol., 227:799-817 (1992).

Co et al., Chimeric and Humanized Antibodies with Specificity for the CD33 Antigen, J. Immunol., 148:1149-1154 (1992).

Co et al., Humanized antibodies for antiviral therapy, Proc. Natl. Acad. Sci. USA 88:2869-2873 (1991).

Cone, R.D. and Mulligan, R.C., High-efficiency gene transfer into mammalian cells: Generation of helper-free recombinant retrovirus with broad mammalian host range, Proc. Natl. Acad. Sci. USA, vol. 81, pp. 6349-6353 (1984).

Crowe et al., Vaccine, 2002; 20:S32-S37.

Cruse et al., Illustrated dictionary of immunology, $2^{nd}$ edition. CRC Press, 2003, pp. 341.

Fabrice Le Gall et al., "Di-, tri- and tetrameric single chain FV antibody fragments against human CD19: effect of valency on cell binding", FEBS Letters 453 (1999) 164-168.

Fahey et al., "A Status of immune-based therapies in HIV infection and AIDS", Clinical and Experimental Immunology, vol. 88 (1992), pp. 1-5.

Fang et al. "Antiviral Research", 53(3); pA65 Mar. 2002, Conference/Meeting: Fifteenth International Conference on Antiviral Research, Prague, Czech Republic, Mar. 17-21, 2002.

Fang et al., Viral receptor blockage by multivalent recombinant antibody fusion proteins: inhibiting human rhinovirus (HRV) infection with CFY196. Journal of Antimicrobial Chemotherapy, 2003, 1-3.

Fitzgerald et al., Total Chemical Synthesis and Catalytic Properties of the Enzyme Enantiomers $_L$- and $_D$-4-Oxalocrotonate Tautomerase, J. Am. Chem. Soc., 117:11075-11080 (1995).

Foote and Winter, "Antibody Framework Residues Affecting the Conformation of the Hypervariable Loops," J. Mol. Biol. 224:487-490 (1992).

Fox. J., No Winner against AIDS, Bio/Technology, vol. 12 (Feb. 1994), p. 128.

Gram et al., In vitro selection and affinity maturation of antibodies from a naive combinatorial immunoglobulin library, Proc. Natl. Acad. Sci. USA, vol. 89, pp. 3576-3580 (1992).

Harbury et al., Science, 262: 1401-1407, 1993.

Harris, Biochemical Society Transactions 23:1035-1038, 1995.

Hartman, S. C. and Mulligan, R.C., Two dominant-acting selectable markers for gene transfer studies in mammalian cells, Proc. Natl. Acad. Sci. USA, vol. 85, pp. 8047-8051 (1988).

(56) References Cited

OTHER PUBLICATIONS

Hayden et al., "Phase II, Randomized, Double-blind, Placebo-Controlled Studies of Ruprintrivir Nasal Spray 2-Percent Suspension for Prevention and Treatment of Experimentally Induced Rhinovirus Colds in Healthy Volunteers", Antimicrobial Agents and Chemotherapy, Dec. 2003, vol. 47(12), p. 3907-3916.
Hodits et al., (1995) "An Antibody Fragment from a Phage Display Library Competes for Ligand Binding to the Low Density Lipoprotein Receptor Family and Inhibits Rhinovirus Infection", J. Biol. Chem. 270 (41):24078-24085.
Hofer et al. (1994) "Members of the low density lipoprotein receptor family mediate cell entry of a minor group common cold virus", Proc. Natl. Acad. Sci. USA 91:1839-1842.
Holsworth, Daniel D. et al., "Antisense-designed peptides: A comparative study focusing on possible complements to angiotensin II", Peptide Research, vol. 7, No. 4, 1994, pp. 185-193.
Hurle et al., Current Opinion in Biotechnology 5:428-433, 1994.
Inbar et al., Localization of Antibody-Combining Sites within the Variable Portions of Heavy and Light Chains, Proc. Natl. Acad. Sci. USA, vol. 69, No. 9, pp. 2659-2662 (1972).
Jones et al., Replacing the complementarity-determining regions in a human antibody with those from a mouse, Nature, 321:522-525 (1986).
Kaiser et al., "In vitro activity of pleconaril and AG7088 against selected serotypes and clinical isolates of human rhinoviruses", Antiviral Research 47 (2000) 215-220.
Kamtekar, S. et al., "Protein design by binary patterning of polar and nonpolar amino acids", Science, Dec. 10, 1993, vol. 262, No. 5140. pp. 1680-1685.
Karush, F. et al., "Multivalence and affinity of antibody", Int. Arch. Allergy Appl. Immunol. 45(1-2):130-132 (1973).
Kay et al., Evidence or gene transfer and expression of factor IX in haemophilia B patients treated with an AAV vector, Nature Genetics, 24:257-261 (2000).
Kipriyanov et al., Affinity enhancement of recombinant antibody: formation of complexes with multiple valency by a single-chain Fv fragment-core streptavidin fusion. Protein Engineering (1996) vol. 9, No. 2, pp. 203-211.
Le Calvez et al., Review: Biochemical prevention and treatment of viral infections—A new paradigm in medicine for infectious diseases. Virology Journal, 2004, vol. 1, 1-6.
Lou, Guang X. et al., "Humanization of an anti-ICAM-1 antibody with over 50-fold affinity and functional improvement", Journal of Immunological Methods, 275 (2003) 31-40.
Lowy et al., Isolation of Transforming DNA: Cloning the Hamster aprt Gene, Cell, 22:817-823 (1980).
Mateo et al., "Humanization of a mouse monoclonal antibody that blocks the epidermal growth factor receptor; recovery of antagonistic activity," (1997), Immunotechnology, vol. 3, pp. 71-81.
Nagahira et al., "Humanization of a mouse neutralizing monoclonal antibody against tumor necrosis factor-α (TNF-α)," (1999), Journal of Immunological Methods, vol. 222, pp. 83-92.
Nakai et al., Adeno-Associated Viral Vector-Mediated Gene Transfer of Human Blood Coagulation Factor IX Into Mouse Liver, Blood 91:4600-4607 (1998).
Ockenhouse et al., *Plasmodium falciparum*-infected erythrocytes bind ICAM-1 at a site distinct from LFA-1, MAC-1, and Human Rhinovirus. Cell 68 (1), 1992, pp. 63-69.
Ohtomo et al., "Humanization of Mouse ONS-M21 Antibody With The Aid of Hybrid Variable Regions," (1995) Molecular Immunology, vol. 1, No. 6, pp. 407-416.
Pack et al., Improved Bivalent Miniantibodies, with Identical Avidity as Whole Antibodies, Produced by High Cell Density Fermentation of *Escherichia coli*, Bio/Technology, 11:1271-1277 (1993).
Pack, Peter et al., "Tetravalent miniantibodies with high avidity assembling in *Escherichia coli*", J. Mol. Biol. 246(1):28-34 (1995).
Padlan (1991) Molecular Immunol. 28: 489-498.
Padlan (1994) Molecular Immunol. 31: 169-217.
PCT International Search Report, dated Sep. 8, 2003 for PCT/US 02/23002.
PCT International Search Report, dated Mar. 15, 1999 for PCT/US98/25422.
Pescini et al., Journal of Biological Chemistry, 269(2): 1159-1165, 1994.
Pestov, D.G. et al., "Genetic selection of growth-inhibitory sequences in mammalian cells", Proceedings of the National Academy of Science, vol. 91, No. 26, Dec. 20, 1994.
Presta et al., "Humanization of an Antibody Directed Against IgE," (1993), Journal of Immunology, vol. 151, No. 5, pp. 2623-2632.
Queen et al., A humanized antibody that binds to the interleukin 2 receptor, Proc. Natl. Acad. Sci. USA, vol. 86, pp. 10029-10033 (1989).
Reichmann et al., Reshaping human antibodies for therapy, Nature, 332:323-327 (1988).
Rothstein, Rodney, Chapter 3, DNA cloning, vol. II, A Practical Approach, IRL Press, Washington, D.C., pp. 1-66 (1986) Glover, D.M. ed.
Rudikoff et al., Single amino acid substitution altering antigen-binding specificity. Proc. Natl. Acad. Sci. USA, 1982 vol. 79, pp. 1979-1983.
Saldanha et al., "A single blackmutation in the human kIV framework of a previously unsuccessfully humanized antibody restores the binding activity and increases the secretion in cos cells," (1999). Molecular Immunology, vol. 36, pp. 709-719.
Sandhu, Jasbir S., Protein Engineering of Antibodies, Critical Reviews in Biotechnology, 12:5, 437-462 (1992).
Sarver et al., Bovine Papilloma Virus Deoxyribonucleic Acid: a Novel Eucaryotic Cloning Vector, Molecular and Cellular Biology, 16:486-496 (1981).
Szybalska, E.H. and Szybalski, W., Genetics of Human Cell Lines, IV. DNA-Mediated Heritable Transformation of a Biochemical Trait, Proc. Natl. Acad. Sci. USA, vol. 48, pp. 2026-2034 (1962).
Tempest et al., "Identification of framework residues required to restore antigen binding during reshaping of a monoclonal antibody against the glycoprotein gB of human cytomegalovirus," (1995), Int. J. Biol. Macromol., vol. 17, No. 1, pp. 37-42.
Terskikh et al., "Peptabody": A new type of high avidity binding protein. Proc. Natl. Acad. Sci. USA 94:1663-1668, 1997.
U.S. Office Action dated Jan. 8, 2004 for U.S. Appl. No. 09/555,446.
U.S. Office Action dated May 21, 2004 for U.S. Appl. No. 09/555,446.
U.S. Office Action dated Apr. 11, 2005 for U.S. Appl. No. 09/555,446.
U.S. Office Action dated Jan. 24, 2006 for U.S. Appl. No. 09/555,446.
U.S. Office Action dated Aug. 23, 2006 for U.S. Appl. No. 09/555,446.
U.S. Office Action dated Sep. 20, 2002 for U.S. Appl. No. 09/910,483.
U.S. Office Action dated May 5, 2003 for U.S. Appl. No. 09/910,483.
U.S. Office Action dated May 28, 2004 for U.S. Appl. No. 09/910,483.
U.S. Office Action dated Mar. 10, 2005 for U.S. Appl. No. 09/910,483.
U.S. Office Action dated Mar. 10, 2006 for U.S. Appl. No. 09/910,483.
Verhoeyen et al., Reshaping Human Antibodies: Grafting an Antilysozyme Activity, Science, 239:1534-1536 (1988).
Welply et al. (1996) A Peptide Isolated by Phage Display Binds to ICAM-1 and Inhibits Binding to LFA-1 Proteins: Structure, Function, and Genetics 26:262-270.
Whitlow, M. and Filpula, D., Single-Chain Fv Proteins and Their Fusion Proteins, Methods: A Companion to Methods in Enzymology 2:97-105 (1991).
Wigler et al., Transfer of Purified Herpes Virus Thymidine Kinase Gene to Cultured Mouse Cells, Cell, 11:223-232 (1977).
Winter et al., Immunology Today 14:243-246, 1993.
Casasnovas, et al, Kinetics and thermodynamics of virus binding to receptor, (1995), J Bio Chem, 270(22):13216-13224.
Complaint for Breach of Contract and Other Relief dated Jun. 9, 2009 in Case No. 37-2000-00003237-CU-BC-CTL filed in Superior Court of the State of California for the County of San Diego.

(56) References Cited

OTHER PUBLICATIONS

Second Amended Complaint for Damages and Other Relief dated Apr. 10, 2007 in Case No. GIC 871276 filed in Superior Court of the State of California for the County of San Diego.

US Notice of Allowance dated Nov. 2, 2009 in related U.S. Appl. No. 11/519,322.

US Office Action dated Feb. 14, 2011 in U.S. Appl. No. 11/710,027.

US Office Action dated Mar. 5, 2009 in related U.S. Appl. No. 11/519,322.

US Office Action dated Jul. 9, 2010 in related U.S. Appl. No. 11/710,027.

NonFinal Office Action dated Mar. 29, 2012 in related U.S. Appl. No. 11/710,027.

Arndt, Helix-stabilized Fv (hsFv) antibody fragments: Substituting the constant domains of a Fab fragment for a heterodimeric coiled-coil domain, Journal of Molecular Biology, London GB, vol. 312, No. 1, 2001, pp. 221-228.

Crameri and Suter, Display of biologically active proteins on the surface of filamentous phages: a cDNA cloning system for selection of functional gene products linked to the genetic information responsible for their production. Gene, 137: 69-75, 1993.

Kalandadze, Expression of recombinant HLA-DR2 molecules. The Journal of Biological Chemistry, 271(33): 20156-20162, 1996.

Kerschaumer, Single-chain Fv fusion proteins suitable as coating and detecting reagents in a double antibody sandwich enzyme-linked immunosorbent assay. Analytical Biochemistry. 249:219-227, 1997.

Kruif and Logtenberg, Leucine zipper dimerized bivalent and bispecitic scFv antibodies from a semi-synthetic antibody phage display library. The Journal of Biological Chemistry, 271(13): 7630-7634, 1996.

Pluckthun and Pack, New protein engineering approaches to multivalent and bispecific antibody fragments. Immunotechnology, 3:83-105, 1997.

Staunton, et al, The arrangement of the immunoglobulin-like domains of ICAM-1 and the binding sited for LFA-1 and rhinovirus, (1990), Cell, 61:243-254.

* cited by examiner

Figure 1. Amino Acid Sequences of Murine 1A6 and Human Consensus Sequences of Heavy Chain Subgroup III (HumIII) and Light Chain κ Subgroup I (Humκ1).

V_H Domain

```
              1                                                        41
Mouse1A6      EVQLQQSGAE LVKPGASLKL SCTASGFNIK DTYIHWMKQR PEQGLEWIGR
              **   **           *       **     **        **    **
HumIII        EVQLVESGGG LVQPGGSLRL SCAASGFNFS ---------- WVRQA PGKGLEWVA--

51 a                                  81 abc             91
Mouse1A6      IDPANDNTTYD PKVQGKATMT ADTSS NTAYL QLNSLTSEDTAVY YCTT
                  *  *     *  *       *  *   *      *    **
HumIII        ---------- A DSVKGRFT IS RDDSKNTAYL QMNSLRAEDTAVY YCTT 103
Mouse1A6      SGYWFA YWGQGTLVT VSS (SEQ ID NO:37)

HumIII        -----WGQGTLVT VSS (SEQ ID NO:39)
```

V_L Domain

```
              1                                                        41                        51
Mouse1A6      DIVLTQSPAT LSVTPGDSVS LSCRASQSIS NNLHWYQQKH SESPRLLKH ASQ
              **       **         * ****                * ****  *
Humκ1         DIQMTQSPSS LSASVGDRVT ITC-------- --- WYQQKP GKAPKLLIY--

61          71          81                                 101
Mouse1A6      SISGIPS RFSGSGSGTD FTLSINSVET EDFGMFFCQQ SNSWPYTFGG GTKLEIKR (SEQ ID NO:38)
                  *   ****** ****          *    ****                *
Humκ1         ----GVPS RFSGSGSGTD FTLTISSLQP EDFATYYC-- ---------- FGQ GTKVEIKR (SEQ ID NO:40)
```

The CDR residues as defined by both Kabat and Chothia are shown in boldface.

Figure 3. Amino Acid Sequences of Murine 1A6, Humanized 1A6 (Hum19), and Human Consensus Sequences of Heavy Chain Subgroup III (Humiii) and Light Chain κI Subgroup I (HumκI). (2 of 2)

V_L Domain

```
              1            11         21          31          41          51
Mouse    DIVLTQSPAT LSVTPGDSVS LSCRASQSIS NNLHWYQQKH SESPRLLIKH ASQ
              **           **    * ***   * ****           *
Hum19    DIQMTQSPSS LSASVGDRVT ITCRASQSIS NNLHWYQQKP GKAPKLLIYH ASQ
                                 * ****            *  ****
HumκI    DIQMTQSPSS LSASVGDRVT ITC------- ------WYQ QKP GKAPKLLIY --  ---

61           71         81           91         101
Mouse    SISGIPS RFSGSGSGTD FTLSINSVET EDFGMFFCQQ SNSWPYTFGG GTKLEIKR  (SEQ ID NO:38)
              *                         ****              *
Hum19    SISGVPS RFSGSGSGTD FTLTISSLQP EDFATYYCQQ SNSWPYTFGQ GTKVEIKR  (SEQ ID NO:44)
HumκI    ---GVPS RFSGSGSGTD FTLTISSLQP EDFATYYC-- ---------- FGQ GTKVEIKR  (SEQ ID NO:40)
```

The CDR residues as defined by both Kabat and Chothia are shown in boldface.

Figure 4. cDNA Sequences of Humanized scFv3 (Hum3)

The restriction sites are underlined. CCATGG NCO I SITE; GGATCC BAMH I SITE; GTTAAC HPA I SITE CGAACCATGGGCGATATCcagatgACCCAATCTCCGtctagcCTGAGCgccAG
TgttGGTgatCGAGTTaccattactTGCCGCGCCAGCCAATCTATCAGTAATAATCTTC
ACTGGTATCAACAAaaaccgggtaaagctCCGaaaCTTCTTATCAAACACGCCTCTCAG
AGCATTAGCGGCgttCCGAGCCGCTTCTCTGGCTCTGGCTCGGGCACGGACTTT
ACCCTTaccATCAGCTCTcttcagccgGAAGACtttGCCaccTATtatTGTCAGCAGTCTAA
TAGCTGGCCGTATACCTTCGGTcaaGGTACCAAGgtcGAGATTAAGCGCGGCGG
TGGCGGTTCTGGTGGCggtggtagcggtggcGGTGGATCCGGTGGCGGTGGCAGCGA
AGTTCAACTTGTTGAGTCTGGTGGCGGTCTGGTTCAGCCGGGTGGCTCTCTGC
GCCTGTCTTGCGCAGCAAGCGGTTTCAACATTAAGGACACCTACATCCATTGG
atgAGGCAAGCTCCGGGTAAGGGTCTGGAGTGGGTGGCACGTATCGACCCGGC
AAACGACAACACCATTTACGATCCGAAGGTGCAGGGCCGTTTTACTatgTCTGC
GGACacCTCTAAGAACACCGCGTACCTTCAGATGAACTCTCTGCGTGCCGAGG
ACACCGCCGTCTACTACTGCACGACCTCTGGCTACTGGTTTGCCTACTGGGGC
CAGGGCACGCTTGTCACCGTCTCTTCTGGTtAaCCC (SEQ ID NO:47)

Figure 5. Protection of HRV15 infection by mouse 1A6 scFv (Ms1) and humanized 1A6 scFv proteins (Hs3, 4, 7, 17, 18, 19 and 21).

SEQUENCE LISTING

```
<160> NUMBER OF SEQ ID NOS: 96

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum A

<400> SEQUENCE: 1

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Ile Tyr Ala Asp Ser Val
    50                  55                  60

Lys Gly Arg Phe Thr Ile Ser Ser Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Asp Ser Gly Tyr Trp Phe Ala Tyr Trp Gly Gln Gly Thr Leu Val
            100                 105                 110

Thr Val Ser Ser
        115

<210> SEQ ID NO 2
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum A

<400> SEQUENCE: 2
gaagttcaac ttgttgagtc tggtggcggt ctggttcagc cgggtggctc tctgcgcctg      60
tcttgcgcag caagcggttt caacattaag gacacctaca tccattgggt gaggcaagct     120
ccgggtaagg gtctggagtg ggtggcacgt atcgacccgg caaacgacaa caccatttac     180
gctgacagcg tgaagggccg ttttactatt tctagcgacg actctaagaa caccgcgtac     240
cttcagatga actctctgcg tgccgaggac accgccgtct actactgcac ggactctggc     300
tactggtttg cctactgggg ccagggcacg cttgtcaccg tctcttct                  348

<210> SEQ ID NO 3
<211> LENGTH: 108
<212> TYPE: PRT
<213> ORGANISM: Artificial Sequence
```

<220> FEATURE:
<223> OTHER INFORMATION: Description of Artificial Sequence: Synthetic
      VL Domain peptide of Hum A

<400> SEQUENCE: 3

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile
        35                  40                  45

Tyr His Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105

<210> SEQ ID NO 4
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum A

<400> SEQUENCE: 4
gatatccaga tgacccaatc tccgtctagc ctgagcgcca gtgttggtga tcgagttacc        60
attacttgcc gcgccagcca atctatcagt aataatcttc actggtatca acaaaaaccg       120
ggtaaagctc cgaaacttct tatctatcac gcctctcaga gcattagcgg cgttccgagc       180
cgcttctctg gctctggctc gggcacggac tttaccctta ccatcagctc tcttcagccg       240
gaagactttg ccacctatta ttgtcagcag tctaatagct ggccgtatac cttcggtcaa       300
ggtaccaagg tcgagattaa gcgc                                              324

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum B

<400> SEQUENCE: 5

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Ile Tyr Ala Asp Ser Val
    50                  55                  60

Lys Gly Arg Phe Thr Ile Ser Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Ala Ser Gly Tyr Trp Phe Ala Tyr Trp Gly Gln Gly Thr Leu Val

```
                    100                 105                 110
Thr Val Ser Ser
        115

<210> SEQ ID NO 6
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum B

<400> SEQUENCE: 6
gaagttcaac ttgttgagtc tggtggcggt ctggttcagc cgggtggctc tctgcgcctg      60
tcttgcgcag caagcggttt caacattaag gacacctaca tccattgggt gaggcaagct     120
ccgggtaagg gtctggagtg ggtggcacgt atcgacccgg caaacgacaa caccatttac     180
gctgacagcg tgaagggccg ttttactatt tctagcgacg actctaagaa caccgcgtac     240
cttcagatga actctctgcg tgccgaggac accgccgtct actactgcac ggcctctggc     300
tactggtttg cctactgggg ccagggcacg cttgtcaccg tctcttct                  348

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum B

<400> SEQUENCE: 7

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Asn
             20                  25                  30

Leu His Trp Tyr Gln Gln Lys Pro Gly Lys Ala Pro Lys Leu Leu Ile
         35                  40                  45

Tyr His Ala Ser Gln Ser Ile Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                 85                  90                  95

Thr Phe Gly Gln Gly Thr Lys Val Glu Ile Lys Arg
            100                 105

<210> SEQ ID NO 8
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum B

<400> SEQUENCE: 8
gatatccaga tgacccaatc tccgtctagc ctgagcgcca gtgttggtga tcgagttacc      60
attacttgcc gcgccagcca atctatcagt aataatcttc actggtatca acaaaaaccg     120
ggtaaagctc cgaaacttct tatctatcac gcctctcaga gcattagcgg cgttccgagc     180
cgcttctctg gctctggctc gggcacggac tttaccctta ccatcagctc tcttcagccg     240
gaagactttg ccaccctatta ttgtcagcag tctaatagct ggccgtatac cttcggtcaa    300
```

```
ggtaccaagg tcgagattaa gcgc                                          324
```

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum C

<400> SEQUENCE: 9

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Asp Pro Ala Asn Asp Asn Thr Ile Tyr Ala Asp Ser Val
     50                  55                  60

Lys Gly Arg Phe Thr Ile Ser Gly Asp Asp Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Thr Ser Gly Tyr Trp Phe Ala Tyr Trp Gly Gln Gly Thr Leu Val
            100                 105                 110

Thr Val Ser Ser
        115
```

<210> SEQ ID NO 10
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum C

<400> SEQUENCE: 10

```
gaagttcaac ttgttgagtc tggtggcggt ctggttcagc cgggtggctc tctgcgcctg     60
tcttgcgcag caagcggttt caacattaag gacacctaca tccattgggt gaggcaagct   120
ccgggtaagg gtctggagtg ggtggcacgt atcgacccgg caaacgacaa caccatttac   180
gctgacagcg tgaagggccg ttttactatt tctggcgacg actctaagaa caccgcgtac   240
cttcagatga actctctgcg tgccgaggac accgccgtct actactgcac gacctctggc   300
tactggtttg cctactgggg ccagggcacg cttgtcaccg tctcttct               348
```

<210> SEQ ID NO 11
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum C

<400> SEQUENCE: 11

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Asn
             20                  25                  30

Leu His Trp Tyr Gln Gln Lys Pro Gly Lys Ala Pro Lys Leu Leu Ile
         35                  40                  45
```

```
Tyr His Ala Ser Gln Ser Ile Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                 85                  90                  95

Thr Phe Gly Gln Gly Thr Lys Val Glu Ile Lys Arg
            100                 105
```

```
<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum C

<400> SEQUENCE: 12
gatatccaga tgacccaatc tccgtctagc ctgagcgcca gtgttggtga tcgagttacc    60
attacttgcc gcgccagcca atctatcagt aataatcttc actggtatca acaaaaaccg   120
ggtaaagctc cgaaacttct tatctatcac gcctctcaga gcattagcgg cgttccgagc   180
cgcttctctg gctctggctc gggcacggac tttacccctta ccatcagctc tcttcagccg   240
gaagactttg ccacctatta ttgtcagcag tctaatagct ggccgtatac cttcggtcaa   300
ggtaccaagg tcgagattaa gcgc                                          324
```

```
<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum D

<400> SEQUENCE: 13

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Asp Pro Ala Asn Asp Asn Thr Ile Tyr Ala Asp Ser Val
         50                  55                  60

Lys Gly Arg Phe Thr Ile Ser Ser Asp Asp Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Thr Ser Gly Tyr Trp Phe Ala Tyr Trp Gly Gln Gly Thr Leu Val
            100                 105                 110

Thr Val Ser Ser
        115
```

```
<210> SEQ ID NO 14
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum D
```

-continued

```
<400> SEQUENCE: 14
gaagttcaac ttgttgagtc tggtggcggt ctggttcagc cgggtggctc tctgcgcctg      60
tcttgcgcag caagcggttt caacattaag gacacctaca tccattgggt gaggcaagct     120
ccgggtaagg gtctggagtg ggtggcacgt atcgacccgg caaacgacaa caccatttac     180
gctgacagcg tgaagggccg ttttactatt tctagcgacg actctaagaa caccgcgtac     240
cttcagatga actctctgcg tgccgaggac accgccgtct actactgcac gacctctggc     300
tactggtttg cctactgggg ccagggcacg cttgtcaccg tctcttct                  348

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum C

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Asn
             20                  25                  30

Leu His Trp Tyr Gln Gln Lys Pro Gly Lys Ala Pro Lys Leu Leu Ile
         35                  40                  45

Tyr His Ala Ser Gln Ser Ile Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                 85                  90                  95

Thr Phe Gly Gln Gly Thr Lys Val Glu Ile Lys Arg
            100                 105

<210> SEQ ID NO 16
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum D

<400> SEQUENCE: 16
gatatccaga tgacccaatc tccgtctagc ctgagcgcca gtgttggtga tcgagttacc      60
attacttgcc gcgccagcca atctatcagt aataatcttc actggtatca acaaaaaccg     120
ggtaaagctc cgaaacttct tatctatcac gcctctcaga gcattagcgg cgttccgagc     180
cgcttctctg gctctggctc gggcacggga tttaccctta ccatcagctc tcttcagccg     240
gaagactttg ccacctatta ttgtcagcag tctaatagct ggccgtatac cttcggtcaa     300
ggtaccaagg tcgagattaa gcgc                                            324

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum E

<400> SEQUENCE: 17
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Ile Tyr Asp Pro Lys Val
    50                  55                  60

Gln Gly Arg Phe Thr Ile Ser Ala Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Thr Ser Gly Tyr Trp Phe Ala Tyr Trp Gly Gln Gly Thr Leu Val
            100                 105                 110

Thr Val Ser Ser
        115

<210> SEQ ID NO 18
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum E

<400> SEQUENCE: 18
gaagttcaac ttgttgagtc tggtggcggt ctggttcagc cgggtggctc tctgcgcctg      60
tcttgcgcag caagcggttt caacattaag gacacctaca tccattgggt gaggcaagct     120
ccgggtaagg gtctggagtg gtggcacgt atcgacccgg caaacgacaa caccatttac     180
gatccgaagg tgcagggccg ttttactatt tctgcggacg actctaagaa caccgcgtac     240
cttcagatga actctctgcg tgccgaggac accgccgtct actactgcac gacctctggc     300
tactggtttg cctactgggg ccagggcacg cttgtcaccg tctcttct                 348

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum E

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile
        35                  40                  45

Tyr His Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105

```
<210> SEQ ID NO 20
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum E

<400> SEQUENCE: 20
gatatccaga tgacccaatc tccgtctagc ctgagcgcca gtgttggtga tcgagttacc       60
attacttgcc gcgccagcca atctatcagt aataatcttc actggtatca acaaaaaccg      120
ggtaaagctc cgaaacttct tatctatcac gcctctcaga gcattagcgg cgttccgagc      180
cgcttctctg gctctggctc gggcacggac tttaccctta ccatcagctc tcttcagccg      240
gaagactttg ccacctatta ttgtcagcag tctaatagct ggccgtatac cttcggtcaa      300
ggtaccaagg tcgagattaa gcgc                                             324

<210> SEQ ID NO 21
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum F

<400> SEQUENCE: 21

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Asp Pro Ala Asn Asp Asn Thr Ile Tyr Ala Asp Ser Val
     50                  55                  60

Lys Gly Arg Phe Thr Ile Ser Ala Asp Asp Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Thr Ser Gly Tyr Trp Phe Ala Tyr Trp Gly Gln Gly Thr Leu Val
            100                 105                 110

Thr Val Ser Ser
        115

<210> SEQ ID NO 22
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum F

<400> SEQUENCE: 22
gaagttcaac ttgttgagtc tggtggcggt ctggttcagc cgggtggctc tctgcgcctg       60
tcttgcgcag caagcggttt caacattaag gacacctaca tccattgggt gaggcaagct      120
ccgggtaagg gtctggagtg gtggcacgt atcgacccgg caaacgacaa caccatttac       180
gctgacagcg tgaagggccg ttttactatt tctgcggacg actctaagaa caccgcgtac      240
cttcagatga actctctgcg tgccgaggac accgccgtct actactgcac gacctctggc      300
tactggtttg cctactgggg ccagggcacg cttgtcaccg tctcttct                   348
```

-continued

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum F

<400> SEQUENCE: 23

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile
        35                  40                  45

Tyr His Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105

<210> SEQ ID NO 24
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum F

<400> SEQUENCE: 24
gatatccaga tgacccaatc tccgtctagc ctgagcgcca gtgttggtga tcgagttacc      60
attacttgcc gcgccagcca atctatcagt aataatcttc actggtatca acaaaaaccg     120
ggtaaagctc cgaaacttct tatctatcac gcctctcaga gcattagcgg cgttccgagc     180
cgcttctctg gctctggctc gggcacggac tttacccttc catcagctc tcttcagccg      240 gaagactttg ccacctatta ttgtcagcag tctaatagct ggccgtatac cttcggtcaa     300
ggtaccaagg tcgagattaa gcgc                                             324

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum G

<400> SEQUENCE: 25

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Ile Tyr Ala Asp Ser Val
    50                  55                  60

Lys Gly Arg Phe Thr Ile Ser Ala Asp Asp Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Thr Thr Ser Gly Tyr Trp Phe Ala Tyr Trp Gly Gln Gly Thr Leu Val
            100                 105                 110

Thr Val Ser Ser
        115

<210> SEQ ID NO 26
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum G

<400> SEQUENCE: 26
gaagttcaac ttgttgagtc tggtggcggt ctggttcagc cgggtggctc tctgcgcctg    60
tcttgcgcag caagcggttt caacattaag gacacctaca tccattgggt gaggcaagct   120
ccgggtaagg gtctggagtg ggtggcacgt atcgacccgg caaacgacaa caccatttac   180
gctgacagcg tgaagggccg ttttactatt tctgcggacg actctaagaa caccgcgtac   240
cttcagatga actctctgcg tgccgaggac accgccgtct actactgcac gacctctggc   300
tactggtttg cctactgggg ccagggcacg cttgtcaccg tctcttct                348

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum G

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile
        35                  40                  45

Lys His Ala Ser Gln Ser Ile Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105

<210> SEQ ID NO 28
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum G

<400> SEQUENCE: 28
gatatccaga tgacccaatc tccgtctagc ctgagcgcca gtgttggtga tcgagttacc    60
attacttgcc gcgccagcca atctatcagt aataatcttc actggtatca acaaaaaccg   120
```

```
ggtaaagctc cgaaacttct tatcaaacac gcctctcaga gcattagcgg cgttccgagc      180
cgcttctctg gctctggctc gggcacggac tttacccta ccatcagctc tcttcagccg       240
gaagactttg ccacctatta ttgtcagcag tctaatagct ggccgtatac cttcggtcaa      300
ggtaccaagg tcgagattaa gcgc                                             324
```

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum H

<400> SEQUENCE: 29

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Ile Tyr Asp Pro Lys Val
    50                  55                  60

Gln Gly Arg Phe Thr Ile Ser Ala Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Thr Ser Gly Tyr Trp Phe Ala Tyr Trp Gly Gln Gly Thr Leu Val
            100                 105                 110

Thr Val Ser Ser
        115
```

<210> SEQ ID NO 30
<211> LENGTH: 348
<212> TYPE: DNA
<213> ORGANISM: Artificial Sequence
<220> FEATURE:
<223> OTHER INFORMATION: Description of Artificial Sequence: Synthetic
      VH nucleotide sequence of Hum H

<400> SEQUENCE: 30

```
gaagttcaac ttgttgagtc tggtggcggt ctggttcagc cgggtggctc tctgcgcctg      60
tcttgcgcag caagcggttt caacattaag gacacctaca tccattgggt gaggcaagct     120
ccgggtaagg gtctggagtg ggtggcacgt atcgacccgg caaacgacaa caccatttac     180
gatccgaagg tgcagggccg ttttactatt tctgcggacg actctaagaa caccgcgtac     240
cttcagatga actctctgcg tgccgaggac accgcgtct actactgcac gacctctggc      300
tactggtttg cctactgggg ccagggcacg cttgtcaccg tctcttct                  348
```

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum H

<400> SEQUENCE: 31

```
Asp Ile Gln Met Thr Gln Ser Pro Ser Ser Leu Ser Ala Ser Val Gly
 1               5                  10                  15
```

```
Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile
        35                  40                  45

Lys His Ala Ser Gln Ser Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105

<210> SEQ ID NO 32
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum H

<400> SEQUENCE: 32
gatatccaga tgacccaatc tccgtctagc ctgagcgcca gtgttggtga tcgagttacc      60
attacttgcc gcgccagcca atctatcagt aataatcttc actggtatca acaaaaaccg    120
ggtaaagctc cgaaacttct tatcaaacac gcctctcaga gcattagcgg cgttccgagc    180
cgcttctctg gctctggctc gggcacggac tttacccctta ccatcagctc tcttcagccg    240
gaagactttg ccacctatta ttgtcagcag tctaatagct ggccgtatac cttcggtcaa    300
ggtaccaagg tcgagattaa gcgc                                           324

<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      VH Domain peptide of Hum I

<400> SEQUENCE: 33

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
            20                  25                  30

Tyr Ile His Trp Met Arg Gln Ala Pro Gly Lys Gly Leu Glu Trp Val
        35                  40                  45

Ala Arg Ile Asp Pro Ala Asn Asp Asn Thr Ile Tyr Asp Pro Lys Val
 50                  55                  60

Gln Gly Arg Phe Thr Met Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Thr Thr Ser Gly Tyr Trp Phe Ala Tyr Trp Gly Gln Gly Thr Leu Val
            100                 105                 110

Thr Val Ser Ser
        115

<210> SEQ ID NO 34
<211> LENGTH: 348
<212> TYPE: DNA
```

```
<213> ORGANISM: Artificial Sequence
<220> FEATURE:
<223> OTHER INFORMATION: Description of Artificial Sequence: Synthetic
      VH nucleotide sequence of Hum I

<400> SEQUENCE: 34
gaagttcaac ttgttgagtc tggtggcggt ctggttcagc cgggtggctc tctgcgcctg      60
tcttgcgcag caagcggttt caacattaag gacacctaca tccattggat gaggcaagct     120
ccgggtaagg gtctggagtg ggtggcacgt atcgacccgg caaacgacaa caccatttac     180
gatccgaagg tgcagggccg ttttactatg tctgcggacg actctaagaa caccgcgtac     240
cttcagatga actctctgcg tgccgaggac accgccgtct actactgcac gacctctggc     300
tactggtttg cctactgggg ccagggcacg cttgtcaccg tctcttct                  348

<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      VL Domain peptide of Hum I

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Asn
                20                  25                  30

Leu His Trp Tyr Gln Gln Lys Pro Gly Lys Ala Pro Lys Leu Leu Ile
            35                  40                  45

Lys His Ala Ser Gln Ser Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105

<210> SEQ ID NO 36
<211> LENGTH: 324
<212> TYPE: DNA
<213> ORGANISM: Artificial Sequence
<220> FEATURE:
<223> OTHER INFORMATION: Description of Artificial Sequence: Synthetic
      VL nucleotide sequence of Hum I

<400> SEQUENCE: 36
gatatccaga tgacccaatc tccgtctagc ctgagcgcca gtgttggtga tcgagttacc      60
attacttgcc gcgccagcca atctatcagt aataatcttc actggtatca acaaaaaccg     120
ggtaaagctc cgaaacttct tatcaaacac gcctctcaga gcattagcgg cgttccgagc     180
cgcttctctg gctctggctc gggcacggac tttacccctta ccatcagctc tcttcagccg    240
gaagactttg ccacctatta ttgtcagcag tctaatagct ggccgtatac cttcggtcaa     300
ggtaccaagg tcgagattaa gcgc                                            324

<210> SEQ ID NO 37
<211> LENGTH: 116
<212> TYPE: PRT
<213> ORGANISM: Artificial Sequence
<220> FEATURE:
```

<223> OTHER INFORMATION: Description of Artificial Sequence: Murine 1A6
VH Domain consensus sequence of Heavy Chain Subgroup III (Humiii)

<400> SEQUENCE: 37

Glu Val Gln Leu Gln Gln Ser Gly Ala Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Met Lys Gln Arg Pro Glu Gln Gly Leu Glu Trp Ile
        35                  40                  45

Gly Arg Ile Asp Pro Ala Asn Asp Asn Thr Ile Tyr Asp Pro Lys Val
    50                  55                  60

Gln Gly Lys Ala Thr Met Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Thr Thr Ser Gly Tyr Trp Phe Ala Tyr Trp Gly Gln Gly Thr Leu Val
            100                 105                 110

Thr Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: Description of Artificial Sequence: Murine 1A6
VL Domain consensus sequence of Light Chain K Subgroup I (HumKI)

<400> SEQUENCE: 38

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys His Ser Glu Ser Pro Arg Leu Leu Ile
        35                  40                  45

Lys His Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Phe Phe Cys Gln Gln Ser Asn Ser Trp Pro Tyr
                85                  90                  95

Thr Phe Gly Gly Gly Thr Lys Leu Glu Ile Lys Arg
            100                 105

<210> SEQ ID NO 39
<211> LENGTH: 93
<212> TYPE: PRT
<213> ORGANISM: Artificial Sequence
<220> FEATURE:
<223> OTHER INFORMATION: Description of Artificial Sequence: Human
VH Domain consensus sequence of Heavy Chain Subgroup III (Humiii)

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Trp Val
            20                  25                  30

Arg Gln Ala Pro Gly Lys Gly Leu Glu Trp Val Ala Ala Asp Ser Val
        35                  40                  45

Lys Gly Arg Phe Thr Ile Ser Arg Asp Asp Ser Lys Asn Thr Ala Tyr
            50                  55                  60

Leu Gln Met Asn Ser Leu Arg Ala Glu Asp Thr Ala Val Tyr Tyr Cys
65                  70                  75                  80

Thr Thr Trp Gly Gln Gly Thr Leu Val Thr Val Ser Ser
            85                  90

<210> SEQ ID NO 40
<211> LENGTH: 81
<212> TYPE: PRT
<213> ORGANISM: Artificial Sequence
<220> FEATURE:
<223> OTHER INFORMATION: Description of Artificial Sequence: Human VL
      Domain consensus sequence of Light Chain K Subgroup I (HumKI)

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

Arg

<210> SEQ ID NO 41
<211> LENGTH: 116
<212> TYPE: PRT
<213> ORGANISM: Artificial Sequence
<220> FEATURE:
<223> OTHER INFORMATION: Description of Artificial Sequence: Murine 1A6
      VH Domain consensus sequence of Heavy Chain Subgroup III (Humiii)

<400> SEQUENCE: 41

Glu Val Gln Leu Gln Gln Ser Gly Ala Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Met Lys Gln Arg Pro Glu Gln Gly Leu Glu Trp Ile
        35                  40                  45

Gly Arg Ile Asp Pro Ala Asn Asp Asn Thr Ile Tyr Asp Pro Lys Val
    50                  55                  60

Gln Gly Lys Ala Thr Met Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
            85                  90                  95

Thr Thr Ser Gly Tyr Trp Phe Ala Tyr Trp Gly Gln Gly Thr Leu Val
        100                 105                 110

Thr Val Ser Ser
        115

<210> SEQ ID NO 42
<211> LENGTH: 108
<212> TYPE: PRT
<213> ORGANISM: Artificial Sequence
<220> FEATURE:
<223> OTHER INFORMATION: Description of Artificial Sequence: Murine 1A6

VL Domain consensus sequence of Light Chain K Subgroup I (HumKI)

<400> SEQUENCE: 42

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys His Ser Glu Ser Pro Arg Leu Leu Ile
        35                  40                  45

Lys His Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Phe Phe Cys Gln Gln Ser Asn Ser Trp Pro Tyr
                85                  90                  95

Thr Phe Gly Gly Gly Thr Lys Leu Glu Ile Lys Arg
            100                 105

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Humanized
      1A6 (HumB) VH Domain consensus sequence of Heavy Chain Subgroup
      III (Humiii)

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Ile Tyr Ala Asp Ser Val
    50                  55                  60

Lys Gly Arg Phe Thr Ile Ser Ser Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Ala Ser Gly Tyr Trp Phe Ala Tyr Trp Gly Gln Gly Thr Leu Val
            100                 105                 110

Thr Val Ser Ser
115

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Humanized
      1A6 (HumB) VL Domain consensus sequence of Light Chain K
      Subgroup I (HumKI)

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile

```
                      35                  40                  45
Tyr His Ala Ser Gln Ser Ile Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                 85                  90                  95

Thr Phe Gly Gln Gly Thr Lys Val Glu Ile Lys Arg
        100                 105
```

<210> SEQ ID NO 45
<211> LENGTH: 93
<212> TYPE: PRT
<213> ORGANISM: Artificial Sequence
<220> FEATURE:
<223> OTHER INFORMATION: Description of Artificial Sequence: Human VH
      Domain consensus sequence of Heavy Chain Subgroup III (Humiii)

<400> SEQUENCE: 45

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Phe Ser Trp Val
                 20                  25                  30

Arg Gln Ala Pro Gly Lys Gly Leu Glu Trp Val Ala Ala Asp Ser Val
             35                  40                  45

Lys Gly Arg Phe Thr Ile Ser Arg Asp Asp Ser Lys Asn Thr Ala Tyr
 50                  55                  60

Leu Gln Met Asn Ser Leu Arg Ala Glu Asp Thr Ala Val Tyr Tyr Cys
 65                  70                  75                  80

Thr Arg Trp Gly Gln Gly Thr Leu Val Thr Val Ser Ser
                 85                  90
```

<210> SEQ ID NO 46
<211> LENGTH: 81
<212> TYPE: PRT
<213> ORGANISM: Artificial Sequence
<220> FEATURE:
<223> OTHER INFORMATION: Description of Artificial Sequence: Human VL
      Domain consensus sequence of Light Chain K Subgroup I (HumKI)

<400> SEQUENCE: 46

```
Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
                 20                  25                  30

Pro Lys Leu Leu Ile Tyr Gly Val Pro Ser Arg Phe Ser Gly Ser Gly
             35                  40                  45

Ser Gly Thr Asp Phe Thr Leu Thr Ile Ser Ser Leu Gln Pro Glu Asp
 50                  55                  60

Phe Ala Thr Tyr Tyr Cys Phe Gly Gln Gly Thr Lys Val Glu Ile Lys
 65                  70                  75                  80

Arg
```

<210> SEQ ID NO 47
<211> LENGTH: 753
<212> TYPE: DNA
<213> ORGANISM: Artificial Sequence
<220> FEATURE:
<223> OTHER INFORMATION: Description of Artificial Sequence: Synthetic
      nucleotide sequence of Humanized scFv3 (Hum3)

```
<400> SEQUENCE: 47
cgaaccatgg gcgatatcca gatgacccaa tctccgtcta gcctgagcgc cagtgttggt    60
gatcgagtta ccattacttg ccgcgccagc caatctatca gtaataatct tcactggtat   120
caacaaaaac cgggtaaagc tccgaaactt cttatcaaac acgcctctca gagcattagc   180
ggcgttccga gccgcttctc tggctctggc tcgggcacgg actttaccct taccatcagc   240
tctcttcagc cggaagactt tgccacctat tattgtcagc agtctaatag ctggccgtat   300
accttcggtc aaggtaccaa ggtcgagatt aagcgcggcg gtggcggttc tggtggcggt   360
ggtagcggtg gcgtggatc cggtggcggt ggcagcgaag ttcaacttgt tgagtctggt   420
ggcggtctgg ttcagccggg tggctctctg cgcctgtctt gcgcagcaag cggtttcaac   480
attaaggaca cctacatcca ttggatgagg caagctccgg gtaagggtct ggagtgggtg   540
gcacgtatcg acccggcaaa cgacaacacc atttacgatc cgaaggtgca gggccgtttt   600
actatgtctg cggacacctc taagaacacc gcgtaccttc agatgaactc tctgcgtgcc   660
gaggacaccg ccgtctacta ctgcacgacc tctggctact ggtttgccta ctggggccag   720
ggcacgcttg tcaccgtctc ttctggttaa ccc                                753

<210> SEQ ID NO 48
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide AVL-1

<400> SEQUENCE: 48
cgaaccatgg gcgatatcca gatgacccaa tctccgtcta gcctgagcgc cagtgttggt    60
g                                                                   61

<210> SEQ ID NO 49
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide AVL-2

<400> SEQUENCE: 49
gtgaagatta ttactgatag attggctggc gcggcaagta atggtaactc gatcaccaac    60
actggcgctc ag                                                       72

<210> SEQ ID NO 50
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide AVL-3

<400> SEQUENCE: 50
ctatcagtaa taatcttcac tggtatcaac aaaaaccggg taaagctccg aaacttctta    60
tctatcacgc c                                                        71

<210> SEQ ID NO 51
<211> LENGTH: 68
<212> TYPE: DNA
<213> ORGANISM: Artificial Sequence
<220> FEATURE:
<223> OTHER INFORMATION: Description of Artificial Sequence: Synthetic
``` oligonucleotide AVL-4

<400> SEQUENCE: 51
cccgagccag agccagagaa gcggctcgga acgccgctaa tgctctgaga ggcgtgatag    60
ataagaag                                                             68

<210> SEQ ID NO 52
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide AVL-5

<400> SEQUENCE: 52
ctctggctct ggctcgggca cggactttac ccttaccatc agctctcttc agccggaaga    60
ctttgccacc                                                           70

<210> SEQ ID NO 53
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide AVL-6

<400> SEQUENCE: 53
ccttgaccga aggtatacgg ccagctatta gactgctgac aataataggt ggcaaagtct    60
tccggc                                                               66

<210> SEQ ID NO 54
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide AVL-7

<400> SEQUENCE: 54
gtataccttc ggtcaaggta ccaaggtcga gattaagcgc ggcggtggcg gttctggtgg    60
cggtggtagc g                                                         71

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide AVL-8

<400> SEQUENCE: 55
cgaaccatgg gcgatatcca gatgacccaa tc                                  32

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide AVL-9

<400> SEQUENCE: 56
cggatccacc gccaccgcta ccaccgccac cag                                 33

<210> SEQ ID NO 57
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide AVH-1

<400> SEQUENCE: 57
ggtggcggtg gatccggtgg cggtggcagc gaagttcaac ttgttgagtc tggtggcggt    60
ctggttcagc cgg                                                       73

<210> SEQ ID NO 58
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide AVH-2

<400> SEQUENCE: 58
gtccttaatg ttgaaaccgc ttgctgcgca agacaggcgc agagagccac ccggctgaac    60
cagaccgcca c                                                         71

<210> SEQ ID NO 59
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide AVH-3

<400> SEQUENCE: 59
ggtttcaaca ttaaggacac ctacatccat tgggtgaggc aagctccggg taagggtctg    60
gagtggg                                                              67

<210> SEQ ID NO 60
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide AVH-4

<400> SEQUENCE: 60
ggcccttcac gctgtcagcg taaatggtgt tgtcgtttgc cgggtcgata cgtgccaccc    60
actccagacc cttacc                                                    76

<210> SEQ ID NO 61
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide AVH-5

<400> SEQUENCE: 61
cgctgacagc gtgaagggcc gttttactat ttctagcgac gactctaaga acaccgcgta    60
ccttcagatg aactctctgc g                                              81

<210> SEQ ID NO 62
<211> LENGTH: 67
<212> TYPE: DNA
<213> ORGANISM: Artificial Sequence
<220> FEATURE:

<223> OTHER INFORMATION: Description of Artificial Sequence: Synthetic
      oligonucleotide AVH-6

<400> SEQUENCE: 62
ccagtagcca gagtccgtgc agtagtagac ggcggtgtcc tcggcacgca gagagttcat    60
ctgaagg                                                              67

<210> SEQ ID NO 63
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide AVH-7

<400> SEQUENCE: 63
ggactctggc tactggtttg cctactgggg ccagggcacg cttgtcaccg tctcttctgg    60
ttaac                                                                65

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide AVH-8

<400> SEQUENCE: 64
ggtggcggtg gatccggt                                                  18

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide AVH-9

<400> SEQUENCE: 65
gggttaacca gaagagacgg                                                20

<210> SEQ ID NO 66
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide BVH-6

<400> SEQUENCE: 66
ccagtagcca gaggccgtgc agtagtagac ggcggtgtcc tcggcacgca gagagttcat    60
ctgaagg                                                              67

<210> SEQ ID NO 67
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide BVH-7

<400> SEQUENCE: 67
ggcctctggc tactggtttg cctactgggg ccagggcacg cttgtcaccg tctcttctgg    60
ttaac                                                                65

<210> SEQ ID NO 68
<211> LENGTH: 81
<212> TYPE: DNA
<213> ORGANISM: Artificial Sequence
<220> FEATURE:
<223> OTHER INFORMATION: Description of Artificial Sequence: Synthetic
    oligonucleotide CVH-5

<400> SEQUENCE: 68
cgctgacagc gtgaagggcc gttttactat ttctggcgac gactctaaga acaccgcgta    60
ccttcagatg aactctctgc g    81

<210> SEQ ID NO 69
<211> LENGTH: 67
<212> TYPE: DNA
<213> ORGANISM: Artificial Sequence
<220> FEATURE:
<223> OTHER INFORMATION: Description of Artificial Sequence: Synthetic
    oligonucleotide CVH-6

<400> SEQUENCE: 69
ccagtagcca gaggtcgtgc agtagtagac ggcggtgtcc tcggcacgca gagagttcat    60
ctgaagg    67

<210> SEQ ID NO 70
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide CVH-7

<400> SEQUENCE: 70
gacctctggc tactggtttg cctactgggg ccagggcacg cttgtcaccg tctcttctgg    60
ttaac    65

<210> SEQ ID NO 71
<211> LENGTH: 67
<212> TYPE: DNA
<213> ORGANISM: Artificial Sequence
<220> FEATURE:
<223> OTHER INFORMATION: Description of Artificial Sequence: Synthetic
    oligonucleotide DVH-6

<400> SEQUENCE: 71
ccagtagcca gaggtcgtgc agtagtagac ggcggtgtcc tcggcacgca gagagttcat    60
ctgaagg    67

<210> SEQ ID NO 72
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide DVH-7

<400> SEQUENCE: 72
gacctctggc tactggtttg cctactgggg ccagggcacg cttgtcaccg tctcttctgg    60
ttaac    65

<210> SEQ ID NO 73
<211> LENGTH: 76
<212> TYPE: DNA
<213> ORGANISM: Artificial Sequence

```
<220> FEATURE:
<223> OTHER INFORMATION: Description of Artificial Sequence: Synthetic
      oligonucleotide EVH-4

<400> SEQUENCE: 73
ggccctgcac cttcggatcg taaatggtgt tgtcgtttgc cgggtcgata cgtgccaccc    60
actccagacc cttacc                                                   76

<210> SEQ ID NO 74
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide EVH-5

<400> SEQUENCE: 74
cgatccgaag gtgcagggcc gttttactat ttctgcggac gactctaaga acaccgcgta    60
ccttcagatg aactctctgc g                                             81

<210> SEQ ID NO 75
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide EVH-6

<400> SEQUENCE: 75
ccagtagcca gaggtcgtgc agtagtagac ggcggtgtcc tcggcacgca gagagttcat    60
ctgaagg                                                             67

<210> SEQ ID NO 76
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide EVH-7

<400> SEQUENCE: 76
gacctctggc tactggtttg cctactgggg ccagggcacg cttgtcaccg tctcttctgg    60
ttaac                                                               65

<210> SEQ ID NO 77
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide FVH-6

<400> SEQUENCE: 77
ccagtagcca gaggtcgtgc agtagtagac ggcggtgtcc tcggcacgca gagagttcat    60
ctgaagg                                                             67

<210> SEQ ID NO 78
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide FVH-7

<400> SEQUENCE: 78
```

```
gacctctggc tactggtttg cctactgggg ccagggcacg cttgtcaccg tctcttctgg    60
ttaac                                                                65

<210> SEQ ID NO 79
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide GVL-3

<400> SEQUENCE: 79
ctatcagtaa taatcttcac tggtatcaac aaaaaccggg taaagctccg aaacttctta    60
tcaaacacgc c                                                         71

<210> SEQ ID NO 80
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide GVL-4

<400> SEQUENCE: 80
cccgagccag agccagagaa gcggctcgga acgccgctaa tgctctgaga ggcgtgaaag    60
ataagaag                                                             68

<210> SEQ ID NO 81
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide GVH-5

<400> SEQUENCE: 81
cgctgacagc gtgaagggcc gttttactat ttctgcggac gactctaaga acaccgcgta    60
ccttcagatg aactctctgc g                                              81

<210> SEQ ID NO 82
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide GVH-6

<400> SEQUENCE: 82
ccagtagcca gaggtcgtgc agtagtagac ggcggtgtcc tcggcacgca gagagttcat    60
ctgaagg                                                              67

<210> SEQ ID NO 83
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide GVH-7

<400> SEQUENCE: 83
gacctctggc tactggtttg cctactgggg ccagggcacg cttgtcaccg tctcttctgg    60
ttaac                                                                65
```

<210> SEQ ID NO 84
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide HVL-3

<400> SEQUENCE: 84
ctatcagtaa taatcttcac tggtatcaac aaaaaccggg taaagctccg aaacttctta    60
tcaaacacgc c    71

<210> SEQ ID NO 85
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide HVL-4

<400> SEQUENCE: 85
cccgagccag agccagagaa gcggctcgga acgccgctaa tgctctgaga ggcgtgaaag    60
ataagaag    68

<210> SEQ ID NO 86
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide HVH-4

<400> SEQUENCE: 86
ggccctgcac cttcggatcg taaatggtgt tgtcgtttgc cgggtcgata cgtgccaccc    60
actccagacc cttacc    76

<210> SEQ ID NO 87
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide HVH-5

<400> SEQUENCE: 87
cgatccgaag gtgcagggcc gttttactat ttctgcggac gactctaaga acaccgcgta    60
ccttcagatg aactctctgc g    81

<210> SEQ ID NO 88
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide HVH-6

<400> SEQUENCE: 88
ccagtagcca gaggtcgtgc agtagtagac ggcggtgtcc tcggcacgca gagagttcat    60
ctgaagg    67

<210> SEQ ID NO 89
<211> LENGTH: 65
<212> TYPE: DNA
<213> ORGANISM: Artificial Sequence

```
<220> FEATURE:
<223> OTHER INFORMATION: Description of Artificial Sequence: Synthetic
      oligonucleotide HVH-7

<400> SEQUENCE: 89
gacctctggc tactggtttg cctactgggg ccagggcacg cttgtcaccg tctcttctgg     60
ttaac                                                                 65

<210> SEQ ID NO 90
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide IVL-3

<400> SEQUENCE: 90
ctatcagtaa taatcttcac tggtatcaac aaaaaccggg taaagctccg aaacttctta     60
tcaaacacgc c                                                          71

<210> SEQ ID NO 91
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide IVL-4

<400> SEQUENCE: 91
cccgagccag agccagagaa gcggctcgga acgccgctaa tgctctgaga ggcgtgaaag     60
ataagaag                                                              68

<210> SEQ ID NO 92
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide IVH-4

<400> SEQUENCE: 92
ggccctgcac cttcggatcg taaatggtgt tgtcgtttgc cgggtcgata cgtgccaccc     60
actccagacc cttacc                                                     76

<210> SEQ ID NO 93
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide IVH-5

<400> SEQUENCE: 93
cgatccgaag gtgcagggcc gttttactat gtctgcggac acctctaaga acaccgcgta     60
ccttcagatg aactctctgc g                                               81

<210> SEQ ID NO 94
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide IVH-6

<400> SEQUENCE: 94
```

```
ccagtagcca gaggtcgtgc agtagtagac ggcggtgtcc tcggcacgca gagagttcat    60
ctgaagg                                                              67

<210> SEQ ID NO 95
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide IVH-7

<400> SEQUENCE: 95
gacctctggc tactggtttg cctactgggg ccagggcacg cttgtcaccg tctcttctgg    60
ttaac                                                                65

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 96

Gly Gly Gly Gly Ser Gly Gly Gly Gly Ser Gly Gly Gly Gly Ser Gly
 1               5                  10                  15

Gly Gly Gly Ser
            20
```

HUMANIZED ANTIBODIES

RELATED APPLICATIONS

This application is a divisional application of 11/519,322 filed Sep. 11, 2006, which is a continuation of Ser. No. 09/910,483 filed Jul. 19, 2001, which is a continuation-in-part of 09/555,446, filed on Aug. 16, 2000 as a 371 national stage of PCT/US98/25422 filed on Nov. 30, 1998, which are hereby incorporated in their entireties.

FIELD OF THE INVENTION

The invention relates to humanized antibody compositions and methods of making and using humanized antibodies.

BACKGROUND

Monoclonal antibodies have become an important class of therapeutic proteins. However, foreign immunoglobulins used in humans can elicit an anti-globulin response which may interfere with therapy or cause allergic or immune complex hypersensitivity. To avoid this problem, a monoclonal antibody may be "humanized," and this is typically carried out by CDR grafting.

CDR's, also called hypervariable regions, are present in immunoglobulin light and heavy chains and are flanked by "framework" regions. CDR grafting was first described in Jones et al. ((1986) Nature 321:522-525). In this and later publications, the CDRs of three mouse antibodies were grafted onto the variable domain frameworks of the hunt an immunoglobulin NEW ($V_H$) and REI ($V_L$). The resulting humanized antibodies had the same antigen specificity and a similar affinity as the parental murine monoclonal antibody (mAb) (Jones et al. supra; Verhoeyen et al. (1988) Science 239:1534-1536; Riechmann et al. (1988) Nature 332:323-327; U.S. Pat. No. 5,225,539).

CDR grafting has been described by Queen and coworkers who reported the humanization of four murine monoclonal antibodies (Queen et al. (1989) Proc. Natl. Acad. Sci. USA 86:10029-10033; Co et al. (1991) Proc. Natl. Acad. Sci. USA 88:286'-2873; Co et al. (1992) J. Immunol. 148:1149-1154; and U.S. Pat. Nos. 5,585,089; 5,693,761; and 5,693,762). Murine residues were inserted in the human framework in order to maintain affinity and, in each case the original antigen specificity was maintained. The affinities of the humanized antibodies ranged from ⅓ to 3 times of the parental unmodified murine antibodies.

SUMMARY

The invention provides humanized antibodies that bind ICAM-1. In one embodiment, the antibody is selected from: SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI). Subsequences of antibodies that bind ICAM-1 are provided, for example, single chain, Fab, Fab' and $(Fab)_2$ fragments. In particular aspects, the humanized antibody has greater affinity for ICAM-1 than the parental (non-human) antibody. Variant and modified forms of antibodies that bind ICAM-1 are also provided, for example, antibodies selected from SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI) having one or more amino acid substitutions, insertions or deletions.

The invention also provides humanized antibodies that bind ICAM-1 and inhibit pathogen infection of cells expressing ICAM-1. Such invention antibodies include antibodies that provide greater protection from pathogen infection than parental (non-human) antibody. In particular aspects, a humanized antibody has a protective efficacy at least 2 times greater, 5 times greater, 10 times greater, 20 times greater, 30 times greater than the non-humanized antibody. In other aspects, the pathogen is human rhinovirus (HRV), coxackie A virus, respiratory syncytial virus (RSV), or malaria.

The humanized antibodies of the invention include intact immunoglobulin molecules, comprising 2 full-length heavy chains and 2 full-length light chains, and subsequences that inhibit pathogen infection. Particular subsequences include, for example, single chain, Fab, Fab' or $(Fab)_2$ fragment.

The humanized antibodies of the invention include multispecific or multifunctional antibodies. In one aspect, such an antibody is formed by linking a humanized antibody to one or more identical or different antibodies to form a multimer (e.g. using a linker). Antibody multimers include a homo- or hetero-dimer, trimer, tetramer or any other higher order oligomer. Antibody multimers that include different antibodies are human, humanized or non-human. Multimeric forms include antibody oligomers that form via a multimerization domain (e.g. a human amino acid sequence) or a covalent bond. Antibody multimers that include a multimerization domain further include forms having a linker located between the multimerization domain and the antibody.

The invention additionally provides nucleic acid sequences encoding humanized antibodies, subsequences and modified from thereof (e.g., amin acid additions, deletions or substitutions). Nucleic acid sequences further include expression cassettes in which nucleic acid encoding humanized antibodies are operably linked to an expression control element. Vectors and cells (prokaryotic and eukaryotic) that include the nucleic acids also are provided.

The invention further provides pharmaceutical compositions including humanized antibodies, subsequences, multimers, variants and modified forms, and nucleic acids encoding them, and a pharmaceutically acceptable carrier. In particular aspects, the pharmaceutically acceptable carrier is compatible with inhalation or nasal delivery to a subject.

The invention further provides methods of inhibiting pathogen infection of a cell. In one embodiment, a method includes contacting a pathogen or a cell with an amount of a humanized antibody, subsequence, multimer, variant or modified form sufficient to inhibit pathogen infection of the cell. In one aspect, the cell expresses ICAM-1. In another aspect, the cell (e.g., epithelial cell) is present in a subject.

The invention also provides methods of inhibiting HRV infection of a cell. In one embodiment, a method includes contacting HRV or a cell susceptible to HRV infection with an amount of a humanized antibody, subsequence, multimer, variant or modified form effective to inhibit HRV infection of the cell (e.g., epithelial cell). In one aspect, the cell is present in a subject. In another aspect, the cell is present in a subject having or at risk of having asthma. In yet another aspect, the subject is a newborn or between the ages of 1 to 5, 5 to 10 or 10 to 18. In still another aspect, the antibody, subsequence, multimer, variant or modified form binds to an antigen present on the surface of the cell (e.g., ICAM-1). In various additional aspects, the humanized antibody is administered locally, via inhalation or intranasally.

The invention also provides methods of inhibiting HRV infection, inhibiting HRV progression or treating HRV infection of a subject. In one embodiment, a method includes administering to a subject having or at risk of having HRV infection an amount of a humanized antibody, subsequence, multimer, variant or modified form effective to inhibit HRV infection, inhibit HRV progression or treat HRV infection of the subject. In one aspect, the subject has or is at risk of having asthma. In another aspect, the subject is a newborn or between the ages of 1 to 5, 5 to 10 or 10 to 18. In various additional aspects, the humanized antibody is administered locally, via inhalation or intranasally.

The invention additionally provides methods of decreasing or inhibiting one or more symptoms of the common cold in a subject. In one embodiment, a method includes administering to a subject having a common cold an amount of a humanized antibody, subsequence, multimer, variant or modified form effective to decrease or inhibit one or more symptoms of the common cold in the subject. In one aspect, the subject has or is at risk of having asthma. In another aspect, the subject is a newborn or between the ages of 1 to 5, 5 to 10 or 10 to 18. In various additional aspects, the humanized antibody is administered locally, via inhalation or intranasally.

BRIEF DESCRIPTION OF THE DRAWINGS

FIG. 1 shows the amino acid sequence of the $V_H$ and $V_L$ domains of murine 1A6 antibody (SEQ ID NOs: 37 and 38, respectively) and human consensus sequence of heavy chain subgroup III (Humiii) (SEQ ID NO: 39) and light chain kappa subgroup I (SEQ ID NO: 40). Asterisks denote amino acid differences between human and mouse sequence. CDR amino acids are in bold face.

FIG. 3 shows the amino acid sequences of the $V_H$ domain of murine 1A6 antibody (SEQ ID NO: 37), humanized $V_H$ domain of 1A6 (HumB/Hum19) (SEQ ID NO: 43), and human consensus sequences of heavy chain subgroup III (Humiii) (SEQ ID NO: 39), as well as the $V_L$ domain of murine 1A6 antibody SEQ ID NO: 38), humanized $V_L$ domain of 1A6 (HumB/Hum19) (SEQ ID NO: 44), and light chain kappa subgroup I (SEQ ID NO: 40). Asterisks and bold face amino acids are as previously indicated.

FIG. 4 shows the cDNA sequence of humanized scFV3 (HumA) antibody (SEQ ID NO: 47). Restriction sites are indicated by underlining.

FIG. 5 shows protection from HRV15 infection with mouse 1A6 scFv antibody and humanized 1A6 scFv antibody HumA, HumB, HumC, HumD, HumF, HumH and HumI.

DETAILED DESCRIPTION

Figure 2A:
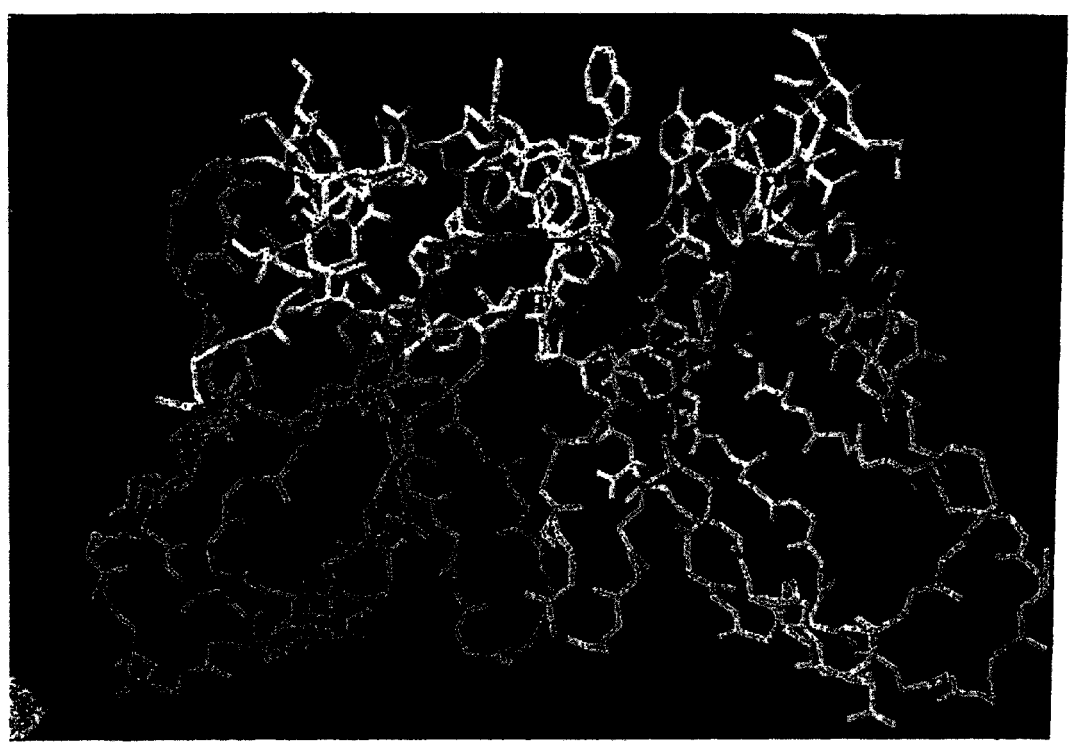
FIG. 2 shows a molecular model of humanized 1A6 (Hum B). (A) side view of humB variable domains which include: $V_H$; $V_L$; CDRs; the six high risk "Vernier zone" residues and the $V_H$60-64. (B) Top view of the humB variable domains which include: $V_H$; $V_L$; CDRs; the six high risk "Vernier zone" residues and the $V_H$60-64.
Figure 2B:
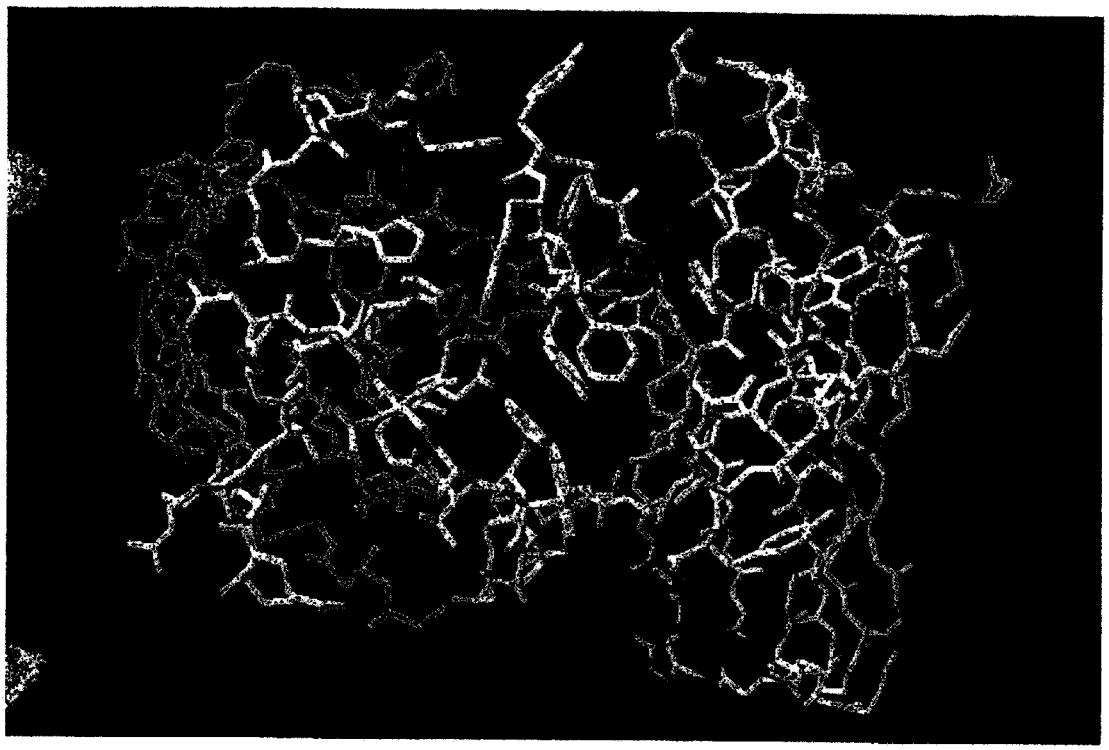

The present invention is based, at least in part, upon producing humanized antibodies. More particularly, complementarity determining region (CDR) from a non-human antibody are grafted into a human framework region. Following grafting, one or more amino acids of the antibody are mutated to human sequences. For example, mutating a murine amino acid to a human amino acid in a framework region or CDR of the grafted antibody can produce a humanized antibody having increased antigen binding affinity relative to the non-human or grafted antibody. Humanized antibodies are not immunogenic or are less immunogenic than non-human antibodies when administered to human subjects. Therefore, humanized antibodies are useful in a variety of therapeutic and diagnostic applications. For example, as exemplified herein, a humanized antibody of the invention protects cells from HRV infection, a virus that can cause the common cold, and other associated disorders (e.g. otitis media, bronchitis, sinusitis etc.).

Thus, in accordance with the invention, there are provided humanized antibodies. In one embodiment, a humanized antibody binds to ICAM-1. In one aspect, a humanized antibody that binds ICAM-1 protects against pathogen infection of cells expressing ICAM-1. In other aspects, a humanized antibody is selected from any of SEQ ID NO:1 and 3 (HumA); SEQ ID NO:5 and 7 (HumB); SEQ ED NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI). In another embodiment, a humanized antibody has a greater or less affinity for the antigen than the donor non-human antibody. In various aspects, affinities range from greater or less affinity for the antigen than either the donor or recombinant antibody. In particular aspects, humanized antibody has an antigen binding affinity 4-fold, 5-fold, 5- to 8-fold, 5- to 10-fold, 8- to 15-fold, 10- to 20-fold, 20- to 40-fold, 20- to 100-fold or greater than the parental antibody.

Human antibody sequence regions can be used for producing humanized antibodies of the invention. For example, a "consensus sequence," an antibody sequence having the most frequently occurring amino acid residues at particular positions in an antibody or an antibody region, may be used. As an example, human variable region domain sequences are described in Kabat (*Sequences of Proteins of Immunological Interest.* 4$^{th}$ Ed. US Department of Health and Human Services. Public Health Service (1987)). Sequences that are completely determined in the framework regions, 1-23, 35-49, and 57-88 in the light chains, and in the framework regions, 1-30, 36-49, and 66-94, in the heavy chains, are included in the survey. For the fourth framework region, 98-107 in the light chain and 103-113 in the heavy chain, residues that can be derived from the known J-minigene segments are surveyed.

At the end of the survey, the most frequently occurring residue at a given position is chosen as the residue in the consensus sequence. Consensus sequences may therefore be identified by surveying amino acid residues at each position of a plurality of antibodies; the most frequently occurring amino acid at a given position in the region of interest is a part of the consensus. In many instances, more than one residue will be found at high frequency at a given position. In such cases, if the amino acid that occurs at least one-fourth as frequently as the most frequently occurring the amino acid residue is considered a part of the consensus sequence.

The published consensus sequence of human $V_H$ subgroup III, based on a survey of 22 known human $V_H$ III sequences, and the published consensus sequence of human $V_L$ kappa-chain subgroup I, based on a survey of 30 known human kappa I sequences may be used for human antibody (Padlan (1994) *Mol. Immunol.* 31:169-217; Padlan (1991) *Mol. Immunol.* 28:489-498). These human consensus sequences were previously used to humanize two antibodies (Carter et al. (1992) *Proc. Natl. Acad. Sci. USA* 89:4285-4289; Presta et al. (1993) *J. Immunol.* 151: 2623-2632). These human $V_H$ subgroup III and $V_L$-kappa subgroup I consensus sequences are selected as frameworks, respectively, to humanize mAb1A6 as described in Example 1. Thus, consensus sequences known in the art, as exemplified for human $V_H$ subgroup III or $V_L$-kappa subgroup I, can be chosen as acceptor frameworks for producing humanized antibody in accordance with the invention.

Any mouse, rat, guinea pig, goat, non-human primate (e.g., ape, chimpanzee, macaque, orangutan, etc.) or other animal antibody may be used as a CDR donor for producing humanized antibody. Murine antibodies secreted by hybridoma cell lines can also be used. Donor CDRs are selected based upon the antigen to which the antibody binds. Thus, donor CDRs include sequences from antibodies that bind to pathogens, such as bacteria, viruses, protozoa and other microorganisms. Donor CDRs also include antibodies that bind to molecules to which the pathogens bind, for example, cell surface proteins (e.g., adhesion proteins, receptor proteins, immune-recognition/modulation proteins such as HLA, tumor associated antigens, etc.). In one particular example, the donor antibody is a mouse monoclonal antibody 1A6 (mAb1A6), which specifically binds to ICAM-1.

"Complementarity determining regions" or "CDRs" are among the sequences that can be grafted into framework sequences. CDRs refer to sequence regions that confer antibody specificity and affinity. CDRs are also generally known as supervariable regions or hypervariable loops. CDR regions of antibodies have been mapped and are defined as in Kabat (*Sequences of Proteins of Immunological Interest.* 4$^{th}$ Ed. US Department of Health and Human Services. Public Health Service (1987)) and Chothia and Lesk ((1987) J. Mol. Biol. 186:651-663)). In particular, for heavy chain, CDR1 is defined as H26-H35, CDR2 is 1150-65 and CDR3 is H95-H102; for light chain, CDR 1 is L24-L34, CDR2 is L50-L56 and CDR3 is L89-L97. The amino acids are numbered according to the scheme described in Kabat (*Sequences of Proteins of Immunological Interest.* 4$^{th}$ Ed. US Department of Health and Human Services. Public Health Service (1987)). Variable region domains typically comprise the amino-terminal approximately 105-115 amino acids a of a naturally-occurring immunoglobulin chain (e.g., amino acids 1-110). Variable domains shorter or longer than these exemplary sequence lengths may also be used.

Thus, the invention provides humanized antibodies, methods of making the antibodies and methods of using the antibodies, including therapeutic and diagnostic methods. In one embodiment, a humanized antibody has increased affinity for the antigen relative to non-humanized antibody (e.g., less than $1.18 \times 10^{-6}$ M in $IC_D$ against ICAM-1; less than $1 \times 10^{-7}$ M in $K_D$ less than $5 \times 10^{-8}$ M in $K_D$, less than $1 \times 10^{-8}$ M in $K_D$ less than $5 \times 10^{-8}$ M in $K_D$). In various aspects, a humanized antibody comprises an amino acid sequence set forth in any of SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI); and antigen binding subsequences thereof. In various additional aspects, an antibody subsequence comprises Fab, Fab', (Fab')$_2$, Fv, and single chain antibody (SCA), e.g., scFv fragments.

The humanized antibodies of the invention also include antibody multimers. In various aspects, a multimer comprises a dimer, trimer, tetramer or other higher order oligomer. In other aspects, multimers comprise combinations of the same antibodies (homo-oligomers) and different antibodies (hetero-oligomers), the different antibodies being human, humanized or non-human.

The terms "protein," "polypeptide" and "peptide" are used interchangeably herein to refer to two or more covalently linked amino acids, also referred to as "residues," through an amide bond or equivalent Polypeptides are of unlimited length and may be comprised of L- or D-amino acids as well as mixtures thereof. Amino acids may be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola (1983) in *Chemistry and Biochemistry of Amino Acids, Peptides and Proteins*, Vol. 7, pp 267-357, "Peptide and Backbone Modifications," Marcel Decker, NY). Polypeptides may have one or more cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids or lipids. Polypeptides further include amino acid structural and functional analogues, for example, peptidomimetics having synthetic or non-natural amino acids or amino acid analogues.

The term "antibody" refers to a protein that binds to other molecules (antigens) via heavy and light chain variable domains, $V_H$ and $V_L$ respectively. Antibodies include IgG, IgD, IgA, IgM and IgE. The antibodies may be intact immunoglobulin molecules, two full length heavy chains linked by disulfide bonds to two full length light chains, as well as subsequences (i.e. fragments) of immunoglobulin molecules, with our without constant region, that bind to an epitope of an antigen, or subsequences thereof (i.e. fragments) of immunoglobulin molecules, with or without constant region, that bind to an epitope of an antigen. Antibodies may comprise full length heavy and light chain variable domains, $V_H$ and $V_L$, individually or in any combination. For example, each of SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI) are included individually and in any combination.

Polypeptide sequences can be made using recombinant DNA technology of polypeptide encoding nucleic acids via cell expression or in vitro translation, or chemical synthesis of polypeptide chains using methods known in the art. Antibodies according to the invention, including humanized sequences and subsequences can be expressed from recombinantly produced antibody-encoding nucleic acid (see, e.g., Harlow and Lane, *Antibodies: A Laboratory Manual*, Cold Spring Harbor Laboratory, 1989; Harlow and Lane, *Using Antibodies: A Laboratory Manual*, Cold Spring Harbor Laboratory, 1999; Fitzgerald et al., *J.A.C.S.* 117:11075 (1995); Gram et al., *Proc. Natl. Acad. Sci. USA* 89:3576-80 (1992)). For example, as described in Example 3, cDNA encoding humanized antibody sequences can be expressed in bacteria in order to produce invention antibodies. Antibodies may also be produced by expressing encoding nucleic acids in mammalian; insect, and plant cells. Polypeptide sequences including antibodies can also be produced by a chemical synthesizer (see, e.g., Applied Biosystems, Foster City, Calif.).

As used herein, the term "subsequence" or "fragment" means a portion of the full length molecule. For example, a subsequence of an antibody is one or more amino acid less in length than full length polypeptide (e.g. one or more internal or terminal amino acid deletions from either amino or carboxy-termini). Subsequences therefore can be any length up to the full length molecule.

Specific examples of antibody subsequences include, for example, Fab, Fab', (Fab')$_2$, Fv, or single chain antibody (SCA) fragment (e.g., scFv). Subsequences include portions which retain at least part of the function or activity of full length sequence. For example, an antibody subsequence will retain the ability to selectively bind to an antigen even though the binding affinity of the subsequence may be greater or less than the binding affinity of the full length antibody. Subsequences can comprise a portion of any of the invention humanized sequences, for example, any of SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI).

Pepsin or papain digestion of whole antibodies can be used to generate antibody fragments. In particular, an Fab fragment consists of a monovalent antigen-binding fragment of an antibody molecule, and can be produced by digestion of a whole antibody molecule with the enzyme papain, to yield a fragment consisting of an intact light chain and a portion of a heavy chain. An (Fab')$_2$ fragment of an antibody can be obtained by treating a whole antibody molecule with the enzyme pepsin, without subsequent reduction. An Fab' fragment of an antibody molecule can be obtained from (Fab')$_2$ by reduction with a thiol reducing agent, which yields a molecule consisting of an intact light chain and a portion of a heavy chain. Two Fab' fragments are obtained per antibody molecule treated in this manner.

An Fv fragment is a fragment containing the variable region of a light chain $V_L$ and the variable region of a heavy chain $V_H$ expressed as two chains. The association may be non-covalent or may be covalent, such as a chemical cross-linking agent or an intermolecular disulfide bond (Inbar et al., (1972) *Proc. Natl. Acad. Sci. USA* 69:2659; Sandhu (1992) *Crit. Rev. Biotech.* 12:437).

A single chain antibody ("SCA") is a genetically engineered or enzymatically digested antibody containing the variable region of a light chain $V_L$ and the variable region of a heavy chain, optionally linked by a flexible linker, such as a polypeptide sequence, in either $V_L$-linker-$V_H$ orientation or in $V_H$-linker-$V_L$ orientation. Alternatively, a single chain Fv fragment can be produced by linking two variable domains via a disulfide linkage between two cysteine residues. Methods for producing scFv antibodies are described, for example, by Whitlow et 4, (1991) In: *Methods: A Companion to Methods in Enzymology* 2:97; U.S. Pat. No. 4,946,778; and Pack et al., (1993) *Bio/Technology* 11:1271.

Other methods of producing antibody subsequences, such as separation of heavy chains to form monovalent light-heavy chain fragments, further cleavage of fragments, or other enzymatic, chemical, or genetic techniques may also be used, provided that the subsequences bind to the antigen to which the intact antibody binds.

As used herein, the term "bind" or "binding" means that the compositions referred to have affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

Invention antibodies, including full length antibodies, subsequences (e.g., single chain forms) may be present as dimer, trimers, tetramers, pentamers, hexamers or any other higher order oligomer that retains at least a part of antigen binding activity of monomer. Multimers can comprise heteromeric or homomeric combinations of full length antibody, subsequences, unmodified or modified as set forth herein and known in the art. Antibody multimers are useful for increasing antigen avidity in comparison to monomer due to the multimer having multiple antigen binding sites. Antibody multimers are also useful for producing oligomeric (e.g., dimer, trimer, tertamer, etc.) combinations of different antibodies thereby producing compositions of antibodies that are multifunctional (e.g., bifunctional, trifunctional, tetrafunctional, etc.).

The term "multifunctional" means that the composition referred to has two or more activities or functions (e.g., antigen binding, enzyme activity, ligand or receptor binding, toxin, etc.). For example, an antibody that binds to a particular antigen which also has an attached polypeptide with enzyme activity (e.g., luciferase, acetyltransferase, galactosidase, peroxidase, etc.) is one particular example of a muiltifunctional antibody.

Multifunctional antibodies further include multispecific (e.g., bispecific, trispecific, tetraspecific, etc.) forms. The term "multispecific" means an antibody that binds to two or more different antigenic epitopes. The term "multispecific" means that the antibody contains two or more variable region sequences that bind to different epitopes. The different epitopes may be present on the same antigen or different antigens. For example, a multispecific antibody oligomer comprises a mixture of two or more antibodies each having different epitope binding specificity and which form a multimer. Multispecific antibodies may be comprised of individual antigen binding polypeptides each of which have distinct variable domains. For example, one of the antibodies may have two variable domains each of which recognizes a different epitope.

Candidate functions for multifunctional antibodies other than antigen binding and in addition to enzyme activity include, for example, detectable moieties such as radioisotopes and amino acid sequences (e.g., $^{35}$S, $^{131}$I, T7, immunoglobulin or polyhistidine tags, toxins (e.g., ricin, cholera, pertussis), cell surface proteins such as receptors, ligands (substrates, agonists and antagonists), adhesion proteins (e.g., streptavidin, avidin, lectins), growth factors, differentiative factors and chemotactic factors.

Multifunctional humanized antibodies can be produced through chemical crosslinking of the selected molecules (which have been produced by synthetic means or by expression of nucleic acid that encode the polypeptides) or through recombinant DNA technology combined with in vitro, or cellular expression of the polypeptide, and subsequent oligomerization. Multispecific antibodies can be similarly produced through recombinant technology and expression, fusion of hybridomas that produce antibodies with different epitopic specificities, or expression of multiple nucleic acid encoding antibody variable chains with different epitopic specificities in a single cell.

Antibodies may be either joined directly or indirectly through covalent or non-covalent binding, e.g. via a multimerization domain, to produce multimers. A "multimerization domain" mediates non-covalent protein-protein interactions. Specific examples include coiled-coil (e.g., leucine zipper structures) and alpha-helical protein sequences. Sequences that mediate protein-protein binding via Van der Waals' forces, hydrogen bonding or charge-charge bonds are also contemplated as multimerization domains. Additional examples include basic-helix-loop-helix domains and other protein sequences that mediate heteromeric or homomeric protein-protein interactions among nucleic acid binding proteins (e.g., DNA binding transcription factors, such as TAFs). One specific example of a multimerization domain is p53 residues 319 to 360 which mediate tetramer formation. Another example is human platelet factor 4, which self-assembles into tetramers. Yet another example is extracellular protein TSP4, a member of the thrombospondin family, which can form pentamers. Additional specific examples are the leucine zippers of jun, fos, and yeast protein GCN4.

Humanized antibodies may be directly linked to each other via a chemical cross linking agent or can be connected via a linker sequence (e.g., a peptide sequence) to form multimers. As used herein, "linker" or "spacer" refers to a molecule or group of molecules that connects two or more molecules to each other. A flexible linker allows rotation of the two molecules linked to each other to the extent that the molecules do not block each others function. For example, a linker such as an amino acid sequence attached to a humanized antibody which is itself attached to a multimerization domain, allows the antibody to bind to antigen without significant steric interference from the multimers of the oligomer. Non-peptide linkers include chemical cross linking agents and polyethylene glycol.

One specific example of a peptide linker is an immunoglobulin hinge sequence. Additional specific examples are polylyisne, ployglutamic acid and mixtures of randomized amino acid sequences. Linker amino acid sequences may be fully human, humanized or non-human amino acid sequences, unmodified or modified as set forth herein. The invention therefore further provides humanized antibodies that include a linker sequence. Linker sequences include, for example, sequences from about 2 to 10, to 20, 10 to 30, 25 to 50, 30 to 60 and 50 to 75 amino acids in length.

Antibodies also include modified forms such as sequences having one or more amino acid substitutions, additions or deletions, provided the modification does not destroy function, e.g., does not destroy antigen binding activity; the antibody retains, at least in part, antigen binding activity. For example, a modified humanized antibody will retain, at least in part, affinity for the antigen to which unmodified antibody binds. The term "modification" therefore denotes an alteration of a molecule that does not destroy an activity of the modified molecule.

Modifications therefore include, for example, amino acid additions, insertions, deletions and substitutions. An example of an addition is where one or more amino acids are added to the N- or C-terminal end of a humanized antibody. An example of an insertion is where an amino acid is inserted into the sequence. An example of a deletion is where one or more amino acids are deleted from the N- or C-terminal end, or internally within the sequence.

The invention therefore also provides modified forms of the humanized antibodies, including one or more amino acid additions, insertions, deletions and substitutions. In one embodiment, a humanized antibody has one or more amino acid substitutions of a sequence set forth in SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI), provided that the substituted antibody is capable of antigen binding. In a particular aspect, one or more of the amino acid substitutions are conservative amino acid substitutions. In another aspect, the substitution comprises 1-3, 3-5 or 5-10 amino acids. In yet another aspect, the substitution is with a human amino acid.

Exemplary amino acid substitutions include conservative amino acid substitutions. The term "conservative substitution" means the replacement of one amino acid by a biologically or chemically similar residue. Biologically similar means that the substitution is compatible with biological activity, e.g., for a humanized antibody, antigen binding. Particular examples of conservative substitutions include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Modifications also include derivatized sequences, for example, amino acids in which free amino groups form amine hydrochlorides, p-toluene sulfonyl groups, cabrobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Also included are modifications that confer covalent bonding, for example, a disulfide linkage between two cysteine residues thereby producing a cyclic polypeptide. Modifications can be produced using any of a variety of methods well known in the art (e.g., PCR based sited-directed, deletion and insertion mutagenesis, chemical modification and mutagenesis, cross-linking, etc.).

Modifications also include addition of functional entities such as tags (e.g., polyhistidine, T7, immunoglobulin, etc.), gold particles, covalently or non-covalently attached to the humanized antibodies or subsequences or multimers. Thus, the invention provides modified humanized antibodies having one or more activities (e.g., retain at least part of the antigen binding activity) of unmodified parent antibody. Modifications include radioactive alternatively non-radioactive detectable labels attached to or incorporated into the molecule.

The term "identical" or "identity" means that two or more referenced entities are the same. Thus, where two nucleic acid sequences are identical, they have the same sequence. "Areas of identity" means that a portion of two or more referenced entities are the same. Thus, where two nucleic acid sequences are identical over one or more parts of their sequence, they share identity in these areas. The term "substantial identity" means that the identity is structurally or functionally significant. That is, the identity is such that the molecules are structurally identical or perform the same function (e.g., biological function) even though the molecules differ. Due to variation in the amount of sequence conservation between structurally and functionally related proteins, the amount of sequence identity for substantial identity will depend upon the type of region/domain and its function. For nucleic acid sequences, 50% sequence homology and above may constitute substantial homology. Substantial homology for proteins can be significantly less, for example, as little as 30% sequence homology, but typically is more, e.g., 50%, 60%, 75%, 85% or more.

The extent of identity between two sequences can be ascertained using various computer programs and mathematical algorithms known in the art. Such algorithms that calculate percent sequence identity (homology) generally account for sequence gaps and mismatches over the comparison region. For example, a BLAST (e.g., BLAST 2.0) search algorithm (see, e.g., Altschul et at (1990) *J. Mol. Biol.* 215:403-10, publicly available through NCBI at http:/www.ncbi.nlm.nikgov) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 and the like.

As used herein, the term "isolated," when used as a modifier of invention compositions (e.g., antibodies, subsequences, modified forms, multimers, nucleic acids encoding same, cells, vectors, etc.), means that the compositions are made by the hand of man and are separated from their naturally occurring in vivo environment. Generally, compositions so separated are substantially free of one or more materials with which they normally associate with in nature, for example, one or more protein, nucleic acid, lipid, carbohydrate, cell membrane. An "isolated" antibody can also be "substantially pure" when free of most or all of the materials with which they may normally associate with in nature. Thus, an isolated molecule that also is substantially pure does not include polypeptides or polynucleotides present among millions of other sequences, such as antibodies of an antibody library or nucleic acids in a genomic or cDNA library, for example. Purity can be at least about 60% or more by mass. The purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (nucleic acid and peptide).

The invention also provides nucleic acids encoding invention humanized antibodies, including high affinity humanized antibodies, subsequences, modified forms and multimers thereof. In various embodiments, a nucleic acid encodes a polypeptide set forth in SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI).

As used herein, a "nucleic acid" refers to at least two or more ribo- or deoxy-ribonucleic acid base pairs that are linked through a phosphoester bond or equivalent. Nucleic acids include polynucleotides and polynculeosides. Nucleic acids include single, double or triplex, circular or linear, molecules. A nucleic acid molecule may belong exclusively or in a mixture to any group of nucleotide-containing molecules, as exemplified by, but not limited to, the following groups of nucleic acid molecules: RNA, DNA, cDNA, genomic nucleic acids, non-genomic nucleic acids, naturally occurring and non naturally occurring nucleic acids and synthetic nucleic acids. This includes, by way of example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule."

Nucleic acids can be of any length. Nucleic acid lengths typically range from about 20 to 10 Kb, 10 to 5 Kb, 1 to 5 Kb or less, 1000 to about 500 base pairs or less in length. Nucleic acids can also be shorter, for example, 100 to about 500 base pairs, or from about 12 to 25, 25 to 50, 50 to 100, 100 to 250, or about 250 to 500 base pairs in length.

As a result of the degeneracy of the genetic code, nucleic acids include sequences and subsequences degenerate with respect to nucleic acids that encode SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI), and subsequences thereof. Nucleic acids also include sequences complementary to a sequence that encodes SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (Hump, and subsequences thereof. Nucleic acid subsequences have from about 15 to 25, 25 to 50 or 50 to 100 nucleotides. Such nucleic acids are useful for hybridization to detect the presence or an amount of humanized antibody in a sample (in vitro, cell, culture medium, tissue or organ, serum, in a subject, etc.).

The invention further includes nucleic acids that hybridize at high stringency to nucleic acids that encode SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI), subsequences thereof and nucleic acid sequences complementary thereto. Hybridizing nucleic acids are also useful for detecting the presence or an amount of humanized antibody in a sample.

The term "hybridize" refers to the binding between complementary nucleic acids. Sequences will generally have more than about 50% homology to a nucleic acid that encodes SEQ ID NO:1 or 3 (HumA); SEQ ID NO:5 or 7 (HumB); SEQ ID NO:9 or 11 (HumC); SEQ ID NO:13 or 15 (HumD); SEQ ID NO:17 or 19 (HumE); SEQ ID NO:21 or 23 (HumF); SEQ. ID NO:25 or 27 (HumG); SEQ ID NO:29 or 31 (HumH); and SEQ ID NO:33 or 35 (HumI). The region between related sequences can extend over at least about 30 base pairs, or about 50 base pairs, or about 100 to 200 or more residues.

As is understood by those skilled in the art, the $T_M$ (melting temperature) refers to the temperature at which binding between complementary sequences is no longer stable. For two sequences to bind, the temperature of a hybridization reaction must be less than the calculated $T_M$ for the sequences. The $T_M$ is influenced by the amount of sequence complementarity, length, composition (% GC), type of nucleic acid (RNA vs. DNA), and the amount of salt, detergent and other components in the reaction (e.g., formamide). All of these factors are considered in establishing appropriate hybridization conditions (see, e.g., the hybridization techniques and formula for calculating $T_M$ described in Sambrook et al., 1989, supra).

Typically, wash conditions are adjusted so as to attain the desired degree of hybridization stringency. Thus, hybridization stringency can be determined empirically, for example, by washing under particular conditions, e.g., at low stringency conditions or high stringency conditions. Optimal conditions for selective hybridization will vary depending on the particular hybridization reaction involved. An example of high stringency hybridization conditions are as follows: 2×SSC/0.1% SDS at about 37 EC or 42 EC (hybridization conditions); 0.5×SSC/0.1% SDS at about room temperature (low stringency wash); 0.5×SSC/0.1% SDS at about 42 EC (moderate stringency wash); and 0.1×SSC/0.1% SDS at about 65 EC (high stringency wash).

Nucleic acids of the invention can be produced using various standard cloning and chemical synthesis techniques.

Such techniques include, but are not limited to: 1) nucleic acid amplification, e.g., polymerase chain reaction (PCR), with genomic DNA or cDNA targets using primers (e.g., a degenerate primer mixture) capable of annealing to antibody sequence; 2) chemical synthesis of nucleic acid sequences which can then be cloned into a plasmid, propagated amplified and purified and; 3) computer searches of databases for related sequences. Purity of nucleic acids can be determined through sequencing, gel electrophoresis and the like.

The invention further provides expression cassettes comprising a nucleic acid encoding a humanized antibody operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates transcription and as appropriate, translation of the transcript.

There need not be physical linkage to nucleic acid in order to control expression. Thus, physical linkage is not required for the elements to be operably linked. For example, a minimal element can be linked to a nucleic acid encoding a humanized antibody. A second element that controls expression of an operably linked nucleic acid encoding a protein that functions "in trans" to bind to the minimal element can influence expression of the humanized antibody. Because the second element regulates expression of humanized antibody, the second element is operably linked to the nucleic acid encoding the humanized antibody.

The term "expression control element" refers to nucleic acid that influences expression of an operably linked nucleic acid. Promoters and enhancers are particular non-limiting examples of expression control elements. A "promoter sequence" is a DNA regulatory region capable of initiating transcription of a downstream (3' direction) coding sequence. The promoter sequence includes a minimum number of bases necessary to initiate transcription. Enhancers also regulate gene expression but can function a distance from the transcription start site of the gene to which it is operably linked. Enhancers also function at either 5' or 3' ends of the gene, as well as within the gene (e.g., in introns or coding sequences).

An expression control element can confer expression in a manner that is "constitutive," such that transcription of the operably linked nucleic acid occurs without the presence of a signal or stimuli. Expression control elements can confer expression in a manner that is "regulatable," that is, a signal or stimuli increases or decreases expression of the operably linked nucleic acid. A regulatable element that increases expression of the operably linked nucleic acid in response to a signal or stimuli is also referred to as an "inducible element" A regulatable element that decreases expression of the operably linked nucleic acid in response to a signal or stimuli is referred to as a "repressible element" (i.e., the signal decreases expression such that when the signal, is removed or absent, expression is increased).

Expression control elements include elements active in a particular tissue or cell type, referred to herein as a "tissue-specific expression control elements." Tissue-specific expression control elements are typically active in specific cell or tissue because they are recognized by transcriptional activator proteins, or other regulators of transcription, that are unique to a specific cell or tissue type.

Expression control elements additionally include elements that confer expression at a particular stage of the cell cycle or differentiation. Accordingly, the invention further includes expression control elements that confer constitutive, regulatable, tissue-specific, cell cycle specific, and differentiation stage specific expression.

Expression control elements include full-length nucleic acid sequences, such as native promoter and enhancer elements, as well as subsequences or nucleotide variants thereof (e.g., substituted/mutated or other forms that differ from native sequences) which retain all or part of full-length or non-variant control element function (confer regulation, e.g., retain some amount of inducibility in response to a signal or stimuli).

For bacterial systems, constitutive promoters such as T7 and the hie, as well as inducible promoters such as pL of bacteriophage λ, plac, ptrp, ptac (ptrp-lac hybrid promoter) may be used. In insect cell systems, constitutive or inducible promoters (e.g., ecdysone) may be used. In yeast, constitutive or inducible promoters may be used (see, e.g., Ausubel et al., In: *Current Protocols in Molecular Biology*, Vol. 2, Ch. 13, ed., Greene Publish. Assoc. & Wiley Interscience, 1988; Grant et al., (1987) In: *Methods in Enzymology*, 153, 516-544, eds. Wu & Grossman, 31987, Acad. Press, N.Y.; Glover, *DNA Cloning*, Vol. II, Ch. 3, IRL Press, Wash., D.C., 1986; Bitter (1987) In: *Methods in Enzymology*, 152, 673-684, eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning. A Practical Approach*. Vol. 11, Ch. 3, ed. D. M. Glover, IRL Press, Wash.; D.C., 1986).

For mammalian cells, constitutive promoters of viral or other origins may be used. For example, SV40, or viral long terminal repeats (LTRs) and the like, or inducible promoters derived from the genome of mammalian cells (e.g., metallothionein 11A promoter; heat shock promoter, steroid/thyroid hormone/retinoic acid response elements) or from mammalian viruses (e.g., the adenovirus late promoter; the inducible mouse mammary tumor virus LTR) can be used for expression.

The invention also provides transformed cells and progeny thereof into which a nucleic acid molecule encoding humanized antibody has been introduced by means of recombinant DNA techniques in vitro, ex vivo or in vivo. The transformed cells can be propagated and the introduced nucleic acid transcribed, or encoded protein expressed. It is understood that a progeny cell may not be identical to the parental cell, since there may be mutations that occur during replication. Transformed cells include but are not limited to prokaryotic and eukaryotic cells such as bacteria, fungi, plant, insect, and animal (e.g., mammalian, including human) cells. The cells may be present in culture, in a cell, tissue or organ ex vivo or present in a subject.

The term "transformed" means a genetic change in a cell following incorporation of nucleic acid (e.g., a transgene) exogenous to the cell. Thus, a "transformed cell" is a cell into which, or a progeny of which a nucleic acid Molecule has been introduced by means of recombinant DNA techniques. Cell transformation to produce host cells may be carried out as described herein or using techniques known in the art. Accordingly, methods of producing cells containing the nucleic acids and cells expressing the humanized antibodies of the invention are also provided.

Typically cell transformation employs a vector. The term "vector," refers to, e.g., a plasmid, virus, such as a viral vector, or other vehicle known in the art that can be manipulated by insertion or incorporation of a nucleic acid, for genetic manipulation (i.e., "cloning vectors"), or can be used to transcribe or translate the inserted polynucleotide (i.e., "expression vectors"). Such vectors are useful for introducing nucleic acids, including a nucleic acid that encodes a humanized antibody operably linked with an expression control element, and expressing the encoded protein in vitro (e.g., in solution or in solid phase), in cells or in vivo.

A vector generally contains at least an origin of replication for propagation in a cell. Control elements, including expression control elements as set forth herein, present within a vector, are included to facilitate transcription and translation. The term "expression control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, etc.

Vectors can include a selection marker. As is known in the art, "selection marker" means a gene that allows for the selection of cells containing the gene. "Positive selection" refers to a process whereby only cells that contain the selection marker will survive upon exposure to the positive selection. Drug resistance is one example of a positive selection marker; cells containing the marker will survive in culture medium containing the selection drug, and cells which do not contain the marker will die. Such markers include drug resistance genes such as neo, which confers resistance to G418, hygr, which confers resistance to hygromycin, or puro which confers resistance to puromycin, among others. Other positive selection marker genes include genes that allow identification or screening of cells containing the marker. These genes include genes for fluorescent proteins (GFP), the lacZ gene, the alkaline phosphatase gene, and surface markers such as CD8, among others.

Vectors can contain negative selection markers. "Negative selection" refers to a process whereby cells containing a negative selection marker are killed upon exposure to an appropriate negative selection agent. For example, cells which contain the herpes simplex virus-thymidine kinase (HSV-tk) gene (Wigler et al., *Cell* 11:223 (1977)) are sensitive to the drug gancyclovir (GANC). Similarly, the gpt gene renders cells sensitive to 6-thioxanthine.

Additional selection systems may be used, including, but not limited to the hypoxanthine-guanine phosphoribosyltransferase gene (Szybalska et al., *Proc. Natl. Acad. Sci. USA* 48:2026 (1962)), and the adenine phosphoribosyltransferase (Lowy et al, *Cell* 22:817 (1980)) genes. Additional selectable genes have been described, namely trpB, which allows cells to utilize indole in place of tryptophan; hisD, which allows cells to utilize histinol in place of histidine (Hartman et al., *Proc. Natl. Acad. Set. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory, ed.).

Vectors included are those based on viral vectors, such as retroviral, adeno-associated virus, adenovirus, reovirus, lentivirus, rotavirus genomes, simian virus 40 (SV40) or bovine papilloma virus, etc., modified for introducing and expressing a nucleic acid in a cell (Cone et al., *Proc. Natl. Acad. Sci. USA* 81:6349 (1984)). (Eukaryotic Viral Vectors, Cold Spring Harbor Laboratory, Gluzman ed., 1982; Sarver et al., *Mol. Biol.* 1:486 (1981)). Additional viral vectors useful for expression include parvovirus, rotavirus, Norwalk virus, coronaviruses, paramyxo and rhabdoviruses, togavirus (e.g., sindbis virus and semliki forest virus) and vesicular stomatitis virus.

Mammalian expression systems further include vectors specifically designed for in vivo and ex vivo expression. Such systems include adeno-associated virus (AAV) vectors (U.S. Pat. No. 5,604,090). AAV vectors have previously been shown to provide expression of Factor IX in humans and in mice at levels sufficient for therapeutic benefit (Kay et al., *Nat. Genet.* 24:257 (2000); Nakai et al., *Blood* 91:4600 (1998)). Adenoviral vectors (U.S. Pat. Nos. 5,700,470, 5,731, 172 and 5,928,944), herpes simplex virus vectors (U.S. Pat. No. 5,501,979) and retroviral (e.g., lentivirus vectors are useful for infecting dividing as well as non-dividing cells and foamy virues) vectors (U.S. Pat. Nos. 5,624,820, 5,693,508, 5,665,577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed and also may be used (see, e.g., U.S. Pat. Nos. 5,821,235, 5,786,340 and 6,110,456).

In yeast, vectors that facilitate integration of foreign nucleic acid sequences into a chromosome, via homologous recombination, for example, are known in the art and can be used. Yeast artificial chromosomes (YAC) are typically used when the inserted nucleic acids are too large for more conventional vectors (e.g., greater than about 12 kb).

Introduction of nucleic acid encoding humanized antibody and humanized antibody into target cells can also be carried out by conventional methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolythers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly(methylmethacrolate) microcapsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes.

The use of liposomes for introducing various compositions into cells, including nucleic acids, is known to those skilled in the art (see, e.g., U.S. Pat. Nos. 4,844,904, 5,000,959, 4,863, 740, and 4,975,282). A carrier comprising a natural polymer, or a derivative or a hydrolysate of a natural polymer, described in WO 94/20078 and U.S. Pat. No. 6,096,291, is suitable for mucosal delivery of molecules, such as polypeptides and polynucleotides. Piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, viral and non-viral vector means of delivery into cells or tissue, in vitro, in vivo and ex vivo are included.

The invention further provides kits comprising one or more compositions of the invention, including pharmaceutical formulations, packaged into suitable packaging material. In one embodiment, a kit includes a humanized antibody or subsequence. In another embodiment, a kit includes a nucleic acid encoding humanized antibody or subsequence. In additional embodiments, a kit includes nucleic acids that further include an expression control element; an expression vector; a viral expression vector; an adeno-associated virus expression vector, an adenoviral expression vector, and a retroviral expression vector. In yet an additional embodiment, a kit includes a cell that expresses a humanized antibody or subsequence.

In additional embodiments, a kit includes a label or packaging insert including instructions for expressing a humanized antibody or a nucleic acid encoding a humanized antibody in cells in vitro, in vivo, or ex vivo. In yet additional embodiments, a kit includes a label or packaging insert including instructions for treating a subject (e.g., a subject having or at risk of having asthma) with a humanized antibody or a nucleic acid encoding a humanized antibody in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating the common cold. Kits of the invention therefore can additionally include instructions for using the kit components in a method of the invention.

Instructions can include instructions for practicing any of the methods of the invention described herein. Thus, invention pharmaceutical compositions can be included in a container, pack, or dispenser together with instructions for administration to a subject. Instructions may additionally include indications of a satisfactory clinical endpoint or any adverse symptoms that may occur, or additional information required by the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include control components for assaying for activity, e.g., a control sample or a standard. Each component of the kit can be enclosed within an individual container or in a mixture and all of the various containers can be within single or multiple packages. For example, an invention composition can be packaged into a hand pump container or pressurized (e.g., aerosol) container for spraying the composition into the throat or nasal or sinus passages of a subject.

The humanized antibodies of the invention, including subsequences, modified forms, multimers and nucleic acids encoding them, can be incorporated into pharmaceutical compositions. Such pharmaceutical compositions are useful for administration to a subject in vivo or ex vivo, and for providing therapy for a physiological disorder or condition treatable with a humanized antibody.

Pharmaceutical compositions include "pharmaceutically acceptable" and "physiologically acceptable" carriers, diluents or excipients. As used herein the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, of microbead. Supplementary active compounds (e.g., preservatives, antibacterial, antiviral and antifungal agents) can also be incorporated into the compositions.

Pharmaceutical compositions can be formulated to be compatible with a particular local or systemic route of administration. Thus, pharmaceutical compositions include carriers, diluents, or excipients suitable for administration by particular routes.

Specific non-limiting examples of routes of administration for compositions of the invention are inhalation or intranasal delivery. Additional routes include parenteral, e.g., intravenous, intradermal, subcutaneous, oral, transdermal (topical), transmucosal, and rectal administration.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride can be included in the composition. Including an agent which delays absorption, for example, aluminum monostearate and gelatin can prolong absorption of injectable compositions.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients as above. In the case of sterile powders for the preparation of sterile injectable solutions, methods of preparation include, for example, vacuum drying and freeze-drying which yields a powder of the active ingredient plus any additional desired ingredient from a previously sterile-filtered solution thereof.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, or creams as generally known in the art.

Invention humanized antibodies, including subsequences and modified forms and nucleic acids encoding them, can be prepared with carriers that protect against rapid elimination from the body, such as a controlled release formulation or a time delay material such as glyceryl monostearate or glyceryl stearate. The compositions can also be delivered using implants and microencapsulated delivery systems to achieve local or systemic sustained delivery or controlled release.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Additional pharmaceutical formulations appropriate for the compositions for administration in the methods of the invention are known in the art (see, e.g., *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; and *Pharmaceutical Principles of Solid Dosage Forms*, Technonic Publishing Co., Inc., Lancaster, Pa., (1993)).

The pharmaceutical formulations can be packaged in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the pharmaceutical carrier or excipient.

Humanized antibodies of the invention include antibodies that protect against virus infection of cells. For example, HumA, HumB, HumC, HumD, HumF, HumH and HumI protect against HRV infection of cells (FIG. 4). Thus, in another embodiment, the invention provides antibodies that protect against human rhinovirus (HRV) infection of cells. In one embodiment, an antibody has a protective efficacy at least 2 to 5 times greater than the non-humanized antibody. In another embodiment, an antibody has a protective efficacy at least 5 to 10 times greater than the non-humanized antibody. In yet another embodiment, an antibody has a protective efficacy at least 10 to 20 times greater than the non-humanized antibody. In still another embodiment, an antibody has a protective efficacy at least 20 to 30 times greater than the non-humanized antibody.

As used herein, "human rhinovirus" or "HRV" means major and minor group human serotypes of rhinoviruses that have been identified (see, e.g., Hamparian et al., (1987) *Virology* 159:191) and those that are identified later as falling within this class of virus. Major group HRV binds to ICAM-1 and minor group HRV binds low density lipoprotein (LDL) receptor.

As used herein, the term "protective efficacy" is the amount of an antibody which can protect 50% of susceptible cells from infection (i.e. $EC_{50}$). For example, for HRV, protective efficacy in $EC_{50}$) is the amount of antibody that protects 50% of hela cells from HRV infection. Thus, a humanized antibody having a protective efficacy 5 times greater than another antibody (e.g., non-humanized) can be used in an amount 5 fold less than non-humanized antibody while still providing the same degree of protection from infection.

Humanized antibodies of the invention include antibodies that bind to ICAM-1. Although not wishing to be bound by theory, it is believed that antibody binding to ICAM-1 inhibits viral binding or the ability to infect or penetrate the cell thereby inhibiting viral infection or proliferation. Such antibodies are therefore useful for inhibiting pathogens such as viruses (e.g., HRV and coxackie A virus, respiratory syncytial virus (RSV)), bacteria, fungi and protozoa (e.g., malaria) that bind to ICAM-1. Thus, the antibodies are useful for inhibiting HRV infection as well as for inhibiting any microorganism or other pathogens in which ICAM-1 receptor participates. Accordingly, the invention provides antibodies that inhibit pathogen infection of cells where infection is mediated, at least in part, by binding to ICAM-1, and methods for inhibiting pathogen infection of cells where infection is mediated, at least in part, by binding to ICAM-1.

In one embodiment, a method includes contacting a virus or cell with an amount of humanized antibody that binds to ICAM-1 sufficient to inhibit viral infection of the cell. In one aspect, the cell is an epithelial cell. In another embodiment, a method includes administering to a subject an amount of humanized antibody that binds to ICAM-1 sufficient to inhibit viral infection of the subject. In various aspects, the virus is HRV, coxackie A virus and respiratory syncytial virus. In yet another embodiment, a method includes administering to a subject an amount of humanized antibody that binds to ICAM-1 sufficient to inhibit infection of the subject by a pathogen.

The invention also provides methods for inhibiting infection, inhibiting progression or treating a pathogenic infection of a subject. In one embodiment, a method includes administering to a subject having or at risk of having an HRV infection an amount of humanized antibody sufficient to inhibit, inhibit progression or to treat HRV infection of the subject. In another embodiment, a method includes administering to a subject having or at risk of having an coxackie A virus or respiratory syncytial virus infection an amount of humanized antibody sufficient to inhibit infection, inhibit progression or to treat coxackie A virus or respiratory syncytial virus infection of the subject. In still another embodiment, a method includes administering to a subject having or at risk of having malaria an amount of humanized antibody sufficient to inhibit, inhibit progression or to treat malaria of the subject. In various aspects, a humanized antibody is selected from SEQ ID NO:1 and 3 (HumA); SEQ ID NO:5 and 7 (HumB); SEQ ID NO:9 and 11 (HumC); SEQ ID NO:13 and 15 (HumD); SEQ ID NO:17 and 19 (HumE); SEQ ID NO:21 and 23 (HumF); SEQ ID NO:25 and 27 (HumG); SEQ ID NO:29 and 31 (HumH); and SEQ ID NO:33 and 35 (HumI), and antigen binding subsequences thereof.

The invention further provides methods of decreasing or inhibiting one or more symptoms of a pathogen infection (e.g., caused by HRV, coxackie A virus, respiratory syncytial virus or malaria). In one embodiment, a method includes administering to a subject having one or more symptoms associated with HRV, coxackie A virus, respiratory syncytial virus or malaria an amount of a humanized antibody sufficient to decrease or inhibit one or more symptoms associated with HRV, coxackie A virus, respiratory syncytial virus or malaria in the subject. Symptoms decreased or inhibited include, for example, for HRV, one or more of fever, congestion, cough, nasal drip, sore throat, and the like associated with the common cold. In another embodiment, a method includes administering to a subject having otitis media an amount of a humanized antibody sufficient to decrease or inhibit one or more symptoms of otitis media in the subject. In yet another embodiment, a method includes administering to a subject having bronchitis an amount of a humanized antibody sufficient to decrease or inhibit one or more symptoms of bronchitis in the subject. In still another embodiment, a method includes administering to a subject having sinusitis an amount of a humanized antibody sufficient to decrease or inhibit one or more symptoms of sinusitis in the subject. In a further embodiment, a method includes administering to a subject having or at risk of having asthma an amount of a humanized antibody sufficient to decrease or inhibit asthma exacerbation. In one aspect, the humanized antibody is administered locally. In another aspect, the humanized antibody is administered via inhalation or intranasally.

In addition to inhibiting pathogens that function directly or indirectly through ICAM-1, invention humanized antibodies can be used to treat undesirable physiological conditions, such as disease or disorders in which ICAM-1 plays a role. For example, LFA-1 interaction with ICAM-1 participates in inflammation. Thus, an invention antibody may be used to inhibit this interaction thereby modulating (e.g., decrease) local or systemic inflammation. Furthermore, ICAM-1 plays a role in other immune response pathways, cancer and metastasis. Thus, an invention antibody may be used to reduce or prevent organ transplant rejection or autoimmune diseases or cancer or metastasis. Accordingly, the invention provides antibodies that modulate immune responsiveness (e.g., inflammation) and other cellular processes in which ICAM-1 participates and methods for modulating immune response pathways.

The methods of the invention may be practiced prior to infection (i.e. prophylaxis) or after infection, before or after acute or chronic symptoms of the infection or physiological condition or disorder develops (e.g., before organ transplantation). Administering a composition prior to or immediately following development of symptoms may lessen the severity of the symptoms in the subject. Administering a composition prior to development of symptoms in the subject may decrease contagiousness of the subject thereby decreasing the likelihood of other subjects becoming infected from the infected subject.

The term "subject" refers to animals, typically mammalian animals, such as a non-human primate (gorillas, chimpanzees, orangutans, macaques, gibbons), a domestic animal (dogs and cats), a farm animal (horses, cows, goats, sheep, pigs), experimental animal (mouse, rat, rabbit, guinea pig) and humans. Human subjects include adults, and children, for example, newborns and older children, for example, between the ages of 1 and 5, 5 and 10 and 10 and 18. Human subjects may include those having or at risk of having a viral infection, such as HRV, and which develops one or more symptoms of the infection, for example, those typically associated with the common cold. Human subjects include those having or at risk of having asthma, including asthmatics suffering from chronic asthma prior to or following suffering an acute asthma attack. Subjects include disease model animals (e.g., such as mice and non-human primates) for testing in viva efficacy of humanized antibodies of the invention (e.g., an HRV animal model, an asthma animal model, an organ transplant model, an autoimmune disorder model, cancer model, etc.).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a transformed cell" includes a plurality of such cells and reference to "a humanized antibody" can include reference to one or more such cells or antibodies, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes the strategy for humanizing 1A6.

Mouse monoclonal antibody 1A6 (mAb 1 A6) was developed by Colonno et al., and has been shown to bind specifically to ICAM-1 and protect cells against infection by human rhinovirus (HRV) major group (Colonno R J, et al. (1991) European Patent Application #91201243.2; Publication number: 0 459 577 A2, which also describes the sequence of mouse mAb1A6). The parental mouse monoclonal antibody 1A6 was synthesized in the form of scFv. The purified protein, Msc1A6, has an affinity of $1.18\times10^{-6}$ M in $K_D$) against ICAM-1 (Table 4).

To humanize mAb1 A6, selected human VH subgroup III and VL-kappa subgroup I consensus sequences were selected as the acceptor VH and VL frameworks, respectively (Padlan (1994) Molecular Immunol. 31:169-217; Padlan (1991) Molecular Immunol. 28:489-498): These human sequences have previously been used to humanize two antibodies (Carter et al. (1992) Proc. Natl. Acad. Sci. USA 89:4285-4289; Presta et al. (1993) J. Immmol. 151:2623-2632).

Among a total of 82 amino acid residues in the heavy chain framework, the human VH III consensus sequence and mAb1A6 antibody share 56 identical amino acid residues, which amounts to 68.3% identity. Among 81 light chain framework residues, the human κ I consensus sequence and mAb1A6 antibody have 52 amino acid residues in common, which equals to 64.2% identity. (FIG. 1).

Among a total of 55 framework amino acid residues that are different between mAb1A6 and human consensus sequences, 49 of them are either located on the surface of the antibody molecule, or are residues with similar characteristics, therefore human consensus residues can be used to replace mouse residues. The remaining six positions, VH 37, 69, 71, 73, 94 and VL 49, belong to the "Vernier" zone as described by Toote and Winter (1992, J. Mol. Biol. 224:487-499). Because "Vernier" zone residues form a layer underlying the CDRs and may impact on the structure of CDRs and the affinity of the antibody, residues at these positions were chosen based on molecular model building of the antibody (FIG: 2).

VL 49:

Inspection reveals that this position is both at the center of the antibody combining site and at the light chain/heavy chain interface. Substituting an ideal residue at this position can improve antigen binding by both providing additional direct binding contact and by improving the character of the interface. Tyrosine, found in human antibodies at this position, does both. Model building suggests that Y49 can form both Van der Waals and H bond contact with ICAM. Y49 also can interact with heavy chain W102, completing a network of interacting aromatic residues that provide both binding interaction and flexibility at the light chain/heavy chain interface. Therefore, human consensus residue tyrosine at this position is superior to the parental mouse residue lysine.

VH 37:

This residue is at the interface between the light and heavy chains. Comparing to the parental mouse residue methionine, the human consensus residue valine intrudes less on the interface, potentially providing additional flexibility. Flexibility at the interface can enhance binding affinity by increasing conformational adaptability of the antibody.

VH 69:

This residue is packed in the interior of the variable domain. The murine residue, methionine, makes a potentially destabilizing contact with the backbone of a neighboring beta strand. In contrast, the human residue isoleucine packs well in the interior of the protein.

VH 73:

Molecular modeling indicates that the human consensus residue, aspartic acid (D73) can interact with K30 of heavy chain CDR1. Since model building suggests that K30 is not involved directly in antigen binding, this stabilizing change is predicted to be either neutral or beneficial.

VH 71 and VH94:

Structural inspection indicated that both of these positions require a residue with a small side chain for maintenance of proper antibody conformation. Therefore, the human consensus residue at this position, arginine, is not appropriate. Serine and glycine were selected for position 71.

According to Chothia et al., residues at VH94 is related with the canonical structure of H1 or CDR1 (defined as VH26-VH32). The CDR1 of 1A6 belongs to the canonical structure 1 and family 1 (Chothia and Lesk (1987) J. Mol. Biol. 186:651-663; Chothia et al. (1992) J. Mol. Biol. 227: 799-817; Chothia et al. (1989) Nature 342:877-883). Corresponding to this canonical structure, human sequences showed three possible residues at VH94 position: arginine, threonine or alanine (Chothia et al. (1992) J. Mol. Biol. 227: 799-817). Since arginine is not appropriate for this particular antibody, alanine, threonine and another small residue, aspartic acid were chosen.

Finally, molecular model building indicates that a portion of the CDR2 in the VH domain, VH60-64, does not have direct contact with the antigen. Therefore mouse residues at these positions (DPKVQ) can be replaced by human residues ADSVK.

Example 2

This example describes the preparation of several humanized scFv expression constructs.

The humanized scFv A (HumA) cDNA (FIG. 4) containing 750 bb was synthesized using a series of overlapping oligonucleotides. These overlapping oligonucleotides (Table 1) were designed to encode the amino acids of the variable region of the heavy ($V_H$) and light ($V_L$) chains linked by a linker (($G_4$)$_4$) with a Bam H1 site. The heavy chain and light chain were cloned separately in TOPO 2.1 vector. After DNA sequencing conformation, the heavy and light chain were subcloned into expression vector (pBAD/pIII A) to form full length DNA.

The oligonucleotides were first annealed in six groups consisting of oligo AVH1/AVH2, oligo AVH3/AVH4, oligo AVH5/AVH6 for heavy chain, and oligo AVL1/AVL2, oligo AVL3/AVL4, oligo AVL5/AVL6 for the light chain. Each annealed group was extended with the Klenow fragment of DNA polymerase. The annealed and extended products of group 1-3 were pooled with oligo AVH7 as overlapping templates that were amplified via polymerase chain reaction (PCR) using the high-fidelity thermostable DNA polymerase (Roche) with oligo AVH8 and AVH9 as primers. The annealed and extended products of group 4-6 were pooled with oligo AVL7 as overlapping templates that were also amplified via polymerase chain reaction (PCR) using oligo AVL8 and AVL9 as primers. The PCR products were directly inserted into the TA cloning vector pCR2.1-TOPO (Invitrogen) and transferred into TOP10 competent cells. The plasmids with inserts were isolated and sequenced.

The light chain and the heavy chain DNA fragments were isolated from their cloning vector by digestion with Nco I/Bam H I and Bam H I/Hpa I respectively, and cloned into expression vector pBAD/pIII A cutting with Nco I/Sal I (blunted) to be in frame with the carboxy-terminal His tag. Both strands of the expression construct pBAD-HumA was sequenced (MWG Biotech, Inc.).

All other human scFv expression constructs (HumB to H) were made with the same procedure as HumA described above except using different oligonucleotides (Table 1).

For HumB, using BVH6 and BVH7 to replace AVH6 and AVH7; for HumC, using CVH5, CVH6 and CVH7 to replace AVH5, AVH6 and AVH7; for HumD, using DVH6 and DVH7 to replace AVH6 and AVH7; for HumE, using EVH4, EVH5, EVH6 and EVH7 to replace AVH4, AVH5, AVH6 and AVH7; for HumF, using FVH6 and FVH7 to replace AVH6 and AVH7; for HumG, using GVL3, GVL4, GVH5, GVH6 and GVH7 to replace AVL3, AVL4, AVH5, AVH6 and AVH7; for HumH, using HVL3, HVL4, HVH4, HVH5, HVH6 and HVH7 to replace AVL3, AVL4, AVH4, AVH5, AVH6 and AVH7; for HumI, using IVL3, IVL4, IVH4, IVH5, IVH6 and IVH7 to replace AVL3, AVL4, AVH4, AVH5, AVH6 and AVH7.

TABLE 1

Oilgonueleoddes for haumanized scFvs

Oligonucleotides for the light ($V_H$) chain of HumA:

AVL-1
CGAACCATGGGCGATATCCAGATGACCCAATCTCCGTCTAGCCTGAGC
GCCAGTGTTGGTG
(SEQ ID NO: 48)

AVL-2:
GTGAAGATTATTACTGATAGATTGGCTGGCGCGGCAAGTAATGGTAAC
TCGATCACCAACACTGGCGCTCAG
(SEQ ID NO: 49)

AVL-3:
CTATCAGTAATAATCTTCACTGGTATCAACAAAAACCGGGTAAAGCTC
CGAAACTTCTTATCTATCACGCC
(SEQ ID NO: 50)

AVL-4:
CCCGAGCCAGAGCCAGAGAAGCGGCTCGGAACGCCGCTAATGCTCTGA
GAGGCGTGATAGATAAGAAG
(SEQ ID NO: 51)

TABLE 1-continued

Oilgonucleoddes for haumanized scFvs

AVL-8:
CTCTGGCTCTGGCTCGGGCACGGACAAACCCTTACCATCAGCTCTCTT
CAGCCGGAAGACTTTGCCACC
(SEQ ID NO: 52)

AVL-8:
CCTTGACCGAAGGTATACGGCCAGCTATTAGACTGCTGACAATAATAG
GTGGCAAAGTCTTCCGGC
(SEQ ID NO: 53)

AVL-7:
GTATACCTTCGGTCAAGGTACCAAGGTCGAGATTAAGCGCGGCGGTGG
CGGTTCTGGTGGCGGTGGTAGCG
(SEQ ID NO: 54)

AVL-8:
CGAACCATTGGGCGATATCCAGATGACCCAATC
(SEQ ID NO: 55)

AVL-9:
CGGATCCACCGCCACCGCTACCACCGCCACCAG
(SEQ ID NO: 56)

Oligonucleotides for the heavy ($V_H$) chain of HumA:

AVH-1:
GGTGGCGGTGGATCTCCGGTGGCGGTGGCAGCAGAAGTTCAACTTGTT
GAGTCTGGTGGCGGTCTGGTTCAGCCGG
(SEQ ID NO: 57)

AVH-2:
GTCCTTAATGTTGAAACCGCTTGCTGCGCAAGACAGGCGCAGAGAGCC
ACCCGGCTGAACCAGACCGCCAC
(SEQ ID NO: 58)

AVH-3:
GGTTTCAACATTAAGGACACCTACATCCATTGGGTGAGGCAAGCTCCG
GGTAAGGGTCTGGAGTGGG
(SEQ ID NO: 59)

AVH-4:
GGCCCTTCACGCTGTCAGCGTAAATGGTGTTGTCGTTTGCCGGGTCGA
TACGTGCCACCCACTCCAGACCCTTACC
(SEQ ID NO: 60)

AVH-5:
CGCTGACAGCGTGAAGGGCCGTTTTACTATTTCTAGCGACGACTCTAA
GAACACCGCGTACCTTCAGATGAACTCTCTGCG
(SEQ ID NO: 61)

AVH-8:
(SEQ ID NO: 62)
CCAGTAGCCAGAGTCCGTCAGTAGTAGACGGCGGTGTCCTCGGCACG
CAGAGAGTTCATCTGAAGG

AVH-7:
GGACTCTGGCTACTGGTTTGCCTACTGGGGCCAGGGCACGCTTGTCAC
CGTCTCTTCTGGTTAAC
(SEQ ID NO: 63)

AYH-8:
GGTGGCGGTGGATCCGGT
(SEQ ID NO: 64)

AVH-9:
GGGTTAACCAGAAGAGACGG
(SEQ ID NO: 65)

Oligonucleotides for making other human scFv
(Hum B-I):

BVH-6:
CCAGTAGCCAGAGGCCGTGCAGTAGTAGACGGCGGTGTCCTCGGCACG
CAGAGAGTTCATCTGAAGG
(SEQ ID NO: 66)

BVH-7:
GGCCTCTGGCTACTGGTTTGCCTACTGGGGCCAGGGCACGCTTGTCAC
CGTCTCTTCTGGTTAAC
(SEQ ID NO: 67)

CVH-5:
CGCTGACAGCGTGAAGGGCCGTTTTACTATTTCTGGCGACGACTCTAA
GAACACCGCGTACCTTCAGATGAACTCTCTGCG
(SEQ ID NO: 68)

CVH-6:
CCAGTAGCCAGAGGTCGTGCAGTAGTAGACGGCGGTGTCCTCGGCACG
CAGAGAGTTCATCTGAAGG
(SEQ ID NO: 69)

CVH-7:
GACCTAGCCAGAGGTTTGCCTACTGGGGCCAGGGCACGCTTGTCACCG
TCTCTTCTGGTAAC
(SEQ ID NO: 70)

DVH-6:
CCAGTAGCCAGAGGTCGTGCAGTAGTAGACGGCGGTGTCCTCGGCACG
CAGAGAGTTCATCTGAAGG
(SEQ ID NO: 71)

DVH-7:
GACCTCTGGCTACTGGTTTGCCTACTGGGGCCAGGGCACGCTTGTCAC
CGTCTCTTCTGGTTAAC
(SEQ ID NO: 72)

EVH-4:
GGCCCTGCACCTTCGGATCGTAAATGGTGTTGTCGTTTGCCGGGTCGA
TACGTGCCACCCACTCCAGACCCTTACC
(SEQ ID NO: 73)

EVH-5:
CGATCCGAAGGTGCAGGGCCGTTTTACTATTTCTGCGGACGACTCTAA
GAACACCGCGTACCTTCAGATGAACTCTCTGCG
(SEQ ID NO: 74)

EVH-6:
CCAGTAGCCAGAGGTCGTGCAGTAGTAGACGGCGGTGTCCTCGGCACG
CAGAGAGTTCATCTGAAGG
(SEQ ID NO: 75)

EVH-7:
GACCTCTGGCTACTGGTTTGCCTACTGGGGCCAGGGCACGCTTGTCAC
CGTCTCAATGGTTAAC
(SEQ ID NO: 76)

FVH-6:
CCAGTAGCCAGAGGTCGTGCAGTAGTAGACGGCGGTGTCCTCGGCACG
CAGAGAGTTCATCTGAAGG
(SEQ ID NO: 77)

HVF-7:
GACCTCTGGCTACTGGTTTGCCTACTGGGGCCAGGGCACGCTTGTCAC
CGTCTCTTCTGGTTAAC
(SEQ ID NO: 78)

GVL-3:
CTATCAGTAATAATCTTCACTGGTATCAACAAAAACCGGGTAAAGCTC
CGAAACTTCTTATCAAACACGCC
(SEQ ID NO: 79)

GVL-4:
CCCGAGCCAGAGCCAGAGAAGCGGCTCGGAACGCCGCTAATGCTCTGA
GAGGCGTGAAAGATAAGAAG
(SEQ ID NO: 80)

GVH-5:
CGCTGACAGCGTGAAGGGCCGTTTTACTATTTCTGCGGACGACTCTAA
GAACACCGCGTACCTTCAGATGAACTCTCTGCG
(SEQ ID NO: 81)

TABLE 1-continued

Oilgonucleoddes for haumanized scFvs

GVH-8:
CCAGTAGCCAGAGGTCGTGCAGTAGTAGACGGCGGTGTCCTCGGCACG
CAGAGAGTTCATCTGAAGG
(SEQ ID NO: 82)

GVH-7:
GACCTCTGGCTACTGGTTTGCCTACTGGGGCCAGGGCACGCTTGTCAC
CGTCTCTTCTGGTTAAC
(SEQ ID NO: 83)

HVL-3:
CTATCAGTAATAATCTTCACTGGTATCAACAAAAACCGGGTAAAGCTC
CGAAACTTCTTATCAAACACGCC
(SEQ ID NO: 84)

HVL-4:
CCCGAGCCAGAGCCAGAGAAGCGGCTCGGAACGCCGCTAATGCTCTGA
GAGGCGTGAAAGATAAGAAG
(SEQ ID NO: 85)

HVH-4:
GGCCCTGCACCTTCGGATCGTAAATGGTGTTGTCGAAGCCGGGTCGAT
ACGTGCCACCCACTCCAGACCCTTACC
(SEQ ID NO: 86)

HVH-5:
CGATCCGAAGGTGCAGGGCCGTTTTACTAAACTGCGGACGACTCTAAG
AACACCGCGTACCTTCAGATGAACTCTCTGCG
(SEQ ID NO: 87)

HVH-6:
CCAGTAGCCAGAGGTCGTGCAGTAGTAGACGGCGGTGTCCTCGGCACG
CAGAGAGTTCATCTGAAGG
(SEQ ID NO: 88)

HVH-7:
GACCTCTGGCTACTGGTTTGCCTACTGGGGCCAGGGCACGCTTGTCAC
CGTCTCTTCTGGTTAAC
(SEQ ID NO: 89)

IVL-3:
CTATCAGTAATAATCTTCACTGGTATCAACAAAAACCGGGTAAAGCTC
CGAAACTTCTTATCAAACACGCC
(SEQ ID NO: 90)

IVL-4:
CCCGAGCCAGAGCCAGAGAAGCGGCTCGGAACGCCGCTAATGCTCTGA
GAGGCGTGAAAGATAAGAAG
(SEQ ID NO: 91)

IVH-4:
GGCCCTGCACCTTCGGATCGTAAATGGTGTTGTCGTTTGCCGGGTCGA
TACGTGCCACCCACTCCAGACCCTTACC
(SEQ ID NO: 92)

IVH-5:
CGATCCGAAGGTGCAGGGCCGTTTTACTATGTCTGCGGACACCTCTAA
GAACACCGCGTACCTTCAGATGAACTCTCTGCG
(SEQ ID NO: 93)

IVH-6:
CCAGTAGCCAGAGGTCGTGCAGTAGTAGACGGCGGTGTCCTCGGCACG
CAGAGAGTTCATCTGAAGG
(SEQ ID NO: 94)

IVH-7:
GACCTCTGGCTACTGGTTTGCCTACTGGGGCCAGGGCACGCTTGTCAC
CGTCTCTTCTGGTTAAC
(SEQ ID NO: 95)

Molecular model building enabled synthesis of 9 versions of humanized antibodies in the form of scFv (HumA-HumI, summarized in Tables 2 and 3). Four of the humanized antibodies, HumA-HumD, do not have parental mouse framework residues, and five of them, HumE-HumI, contain various number of parental mouse residues in the framework. The sequence of HumB is compared against parental mouse 1A6 and human consensus framework in FIG. 3.

TABLE 2

Humanization Constructs

| Position Human/Mouse | L49 Y/K | H37 V/M | H60-64 ADSVK/DPKVQ | H69 I/M | H71 R/A | H73 D/T | H94 R/T |
|---|---|---|---|---|---|---|---|
| HumA | Y | V | ADSVK | I | S | D | D |
| HumB | Y | V | ADSVK | I | S | D | A |
| HumC | Y | V | ADSVK | I | G | D | T |
| HumD | Y | V | ADSVK | I | S | D | T |
| HumE | Y | V | DPKVQ | I | A | D | T |
| HumF | Y | V | ADSVK | I | A | D | T |
| HumG | K | V | ADSVK | I | A | D | T |
| HumH | K | V | DPKVQ | I | A | D | T |
| HumI | K | M | DPKVQ | M | A | T | T |

TABLE 3

Amino Acid Sequences of Humanized Antibody

Hum A:

vH Domain
Glu Val Gln Leu Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Ala Asp Ser Val Lys Gly) Arg Phe Thr Ile Ser Ser
Asp Asp Ser Lys Asn Thr Ala Tyr Leu Gln Met Asn
Ser Leu Arg Ala Glu Asp Thr Ala Val Tyr Tyr Cys
Thr Asp (Ser Gly Tyr Trp Phe Ala Tyr) Trp Gly Gln
Gly Thr Leu Val Thr Val Ser Ser
(SEQ ID NO: 1)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Tyr (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 3)

Hum B:

VH Domain
Glu Val Gln Leu Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Ala Asp Ser Val Lys Gly) Arg Phe Thr Ile Ser Ser
Asp Asp Ser Lys Asn Thr Ala Tyr Leu Gln Met Asn
Ser Leu Arg Ala Glu Asp Thr Ala Val Tyr Tyr Cys
Thr Ala (Ser Gly Tyr Trp Phe Ala Tyr) Trp Gly Gln
Gly Thr Leu Val Thr Val Ser Ser
(SEQ ID NO: 5)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr TABLE 3 -continued Amino Acid Sequences of Humanized Antibody Gln Gln Lys Pro Gly Lys Ala Pro Lys Leu Leu Ile
Tyr (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 7)

Hum C:

VH Domain
Glu Val Gln Leu Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Ala Asp Ser Val Lys Gly) Arg Phe Thr Ile Ser Gly
Asp Asp Ser Lys Asn Thr Ala Tyr Leu Gln Met Asn
Ser Leu Arg Ala Glu Asp Thr Ala Val Tyr Tyr Cys
Thr Thr (Ser Gly Tyr Trp Phe Ala Tyr) Trp Gly Gln
Gly Thr Leu Val Thr Val Ser Ser
(SEQ ID NO: 9)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Tyr (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 11)

Hum D:

VH Domain
Glu Val Gln Leu Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Ala Asp Ser Val Lys Gly) Arg Phe Thr Ile Ser Ser
Asp Asp Ser Lys Asn Thr Ala Tyr Leu Gln Met Asn
Ser Leu Arg Ala Glu Asp Thr Ala Val Tyr Tyr Cys
Thr Thr (Ser Gly Tyr Trp Phe Ala Tyr) Trp Gly Gln
Gly Thr Leu Val Thr Val Ser Ser
(SEQ ID NO: 13)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Tyr (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 15)

Hum E:

VH Domain
Glu Val Gln Leu Val Glu Ser Gly Gly Gly Leu Val
Gln Pro Gly Gly Set Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Asp Pro Lys Val Gln Gly) Arg Phe Thr Ile Ser Ala
Asp Asp Ser Lys Asn Thr Ala Tyr Leu Gln Met Asn
Ser Leu Arg Ala Glu Asp Thr Ala Val Tyr Tyr Cys
Thr Thr (Ser Gly Tyr Trp Phe Ala Tyr) Trp Gly Gln
Gly Thr Leu Val Thr Val Ser Ser
(SEQ ID NO: 17)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Tyr (His Ala Ser Gln Ser Ile Ser) Gly Val Pro Ser
Arg Phe Ser Gly Ser Gly Ser Gly Thr Asp Phe Thr
Leu Thr Ile Set Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 19)

Hum F:

VH Domain
Glu Val Gln Leu Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Ala Asp Ser Val Lys Gly) Arg Phe Thr Ile Ser Ala
Asp Asp Ser Lys Asn Thr Ala Tyr Leu Gln Met Asn
Ser Leu Arg Ala Glu Asp Thr Ala Val Tyr Tyr Cys
Thr Thr (Ser Gly Tyr Trp Phe Ala Tyr) Trp Gly Gln
Gly Thr Leu Val Thr Val Ser Ser
(SEQ ID NO: 21)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Tyr (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 23)

Hum G:

VH Domain
Glu Val Gln Leu Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr
Ala Asp Ser Val Lys Gly) Arg Phe Thr Ile Ser Ala
Asp Asp Ser Lys Asn Thr Ala Tyr Leu Gln Met Asn
Ser Leu Arg Ala Glu Asp Thr Ala Val Tyr Tyr Cys
Thr Thr (Ser Gly Tyr Trp Phe Ala Tyr) Trp Gly Gln
Gly Thr Leu Val Thr Val Ser Ser
(SEQ ID NO: 25)

VL Domain
Asp Ile Gln Act Thr Gln Ser Pro Ser Set Leu Ser
Ala Ser Val Gly Asp Arg Val Thr Ile Thr Cys (Arg
Ala Ser Gln Ser De Ser Asn Asn Leu His) Trp Tyr
Gln Gln Lys Pro Gly Lys Ala Pro Lys Leu Leu Ile
Lys (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 27)

Hum H:

VH Domain
Glu Val Gln Ley Val Glu Ser Gly Gly Gly Leu Val
Gln Pro Gly Gly Ser Leu Arg Leu Ser Cys Ala Ala
Ser (Gly Phe Asn Ile Lys Asp Thr Tyr Ile His) Trp
Val Arg Gln Ala Pro Gly Lys Gly Leu Glu Trp Val
Ala (Arg Ile Asp Pro Ala Asn Asp Asn Thr Ile Tyr

TABLE 3 -continued

Amino Acid Sequences of Humanized Antibody

```
Asp Pro Lys Val Gln Gly) Arg Phe Thr Ile Ser Ala
Asp Asp Ser Lys Asn Thr Ala Tyr Leu Gln Met Asn
Ser Leu Arg Ala Glu As Thr Ala Val Tyr Tyr Cys Thr
Thr (Ser Gly Tyr Trp Phe Ala Tyr) Trp Gly Gln Gly
Thr Leu Val Thr Val Ser Ser
(SEQ ID NO: 29)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Lys (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 31)
```

Hum I:

```
VH Domain
Glu Val Gln Leu Val Glu Ser Gly Gly Gly Lau Val
Gln Pro Gly Gly Ser Leu Arg Leu Ser Cys Ala Ala
Ser (Gly Phe Asn Ile Lys Asp Thr Tyr Ile His) Trp
Met Arg Gln Ala Pro Gly Lys Gly Leu Glu Trp Val
Ala (Arg Ile Asp Pro Ala Asn Asp Asn Thr Ile Tyr
Asp Pro Lys Val Gln Gly) Arg Phe Thr Met Ser Ala
Asp Thr Ser Lys Asn Thr Ala Tyr Leu Gln Met Asn
Ser Leu Arg Ala Glu Asp Thr Ala Val Tyr Tyr Cys
Thr Thr (Ser Gly Tyr Trp Phe Ala Tyr) Trp Gly Gln
Gly Thr Leu Val Thr Val Ser Ser
(SEQ ID NO: 33)

VL Domain
Asp Ile Gln Met Thr Gln Ser Pro Ser Ser Leu Ser
Ala Ser Val Gly Asp Arg Val Thr Ile Thr Cys (Arg
Ala Ser Gln Ser Ile Ser Asn Asn Leu His) Trp Tyr
Gln Gln Lys Pro Gly Lys Ala Pro Lys Leu Leu Ile
Lys (His Ala Ser Gln Ser Ile Ser) Gly Val Pro Ser
Arg Phe Ser Gly Ser Gly Ser Gly Thr Asp Phe Thr
Leu Thr Ile Ser Ser Leu Gln Pro Glu Asp Phe Ala
Thr Tyr Tyr Cys (Gln Gln Ser Asn Ser Trp Pro Tyr
Thr) Phe Gly Gln Gly Thr Lys Val Glu Ile Lys Arg
(SEQ ID NO: 35)
```

The CDR residues are included within brackets.

Example 3

This example describes expression and purification of humanized 1A6 single chain antibody proteins.

For production of the humanized 1A6 scFv, TOP10 cells transformed with desired expression construct were grown in shaker flasks in TB medium (Bio 101) until they reached an $OD_{600}$ of 0.8. Protein expression was induced with 0.02% arabinose for eighteen hours at room temperature. Cells were pelleted by centrifugation at 4,000 g for 15 minutes. Cell pellets were resuspended in 1/50 volume of lysis buffer (20 mM sodium phosphate, 1% Triton X-100, 500 mM NaCl, 40 mM imidazole, 2 mM 2-mercaptoethanol), 0.2 mM PMSF, lysozyme and incubated on ice for 30 minutes. The cell suspension was sonicated and another aliquot of PMSF was added. The cell debris was pelleted by centrifugation at 12,000×g and the clarified sonicate was filtered and fractionated by metal affinity chromatography. Induced histidine-tagged proteins were bound to a Hi Trap™ metal chelating column (Amersham/Pharmacia) equilibrated with $Ni^{2+}$ according to the manufacturer's instructions. The column was then washed with four column volumes of buffer consisting of 100 mM imidazole, 20 mM sodium phosphate, pH 7.4, 500 mM NaCl. Fractions of proteins eluted from the column in 500 mM Imidazole, 20 mM sodium phosphate, pH 7.4 were collected, pooled and dialyzed at 4° C. against phosphate buffered saline (PBS)/2 mM EDTA, then dialyzed against PBS.

Example 4

This example describes studies measuring binding affinity of humanized single chain antibody proteins for ICAM-1.

To evaluate the binding affinity of histidine-tagged human single chain (hsc) proteins soluble ICAM was used in an ELISA assay. A 96-well EIA plate (Corning, Inc.) was coated with 100 µl/well soluble ICAM-1 (Bender MedSystems) at 1 µg/ml in 0.1 M. $NaHCO_3$. After washing with TBST (50 mM Tris, pH8.0, 150 mM NaCl, 0.05% Tween-20), the plate was blocked with 3% non-fat milk in TBST at 37° C. for 1 hour. After washing with TBST, the plate was incubated with scFv samples (100 µl/well) diluted in 1% non-fat milk/TBST solution at room temperature for 1 hour. After washing with TBST, the horse radish peroxidase-conjugated anti-His (C-term) antibody (Invitrogen) diluted 1:2000 in 1% non-fat milk/TBST was added and the plate was incubated at room temperature for 1 hour. The plate was washed thoroughly with TBST and 100 µl/well 3,3',5,5'-tetramethybenzidine substrate solution (Kirkegaard and Perry Laboratories) was added. After 5 min incubation, the color development was stopped by adding 100 ml/well 0.12 N HCl and the absorbance of the wells at 450 nm was measured by a plate reader (ICN).

Binding studies revealed that all of the humanized scFv proteins (hsc) demonstrate greater than ten times higher binding affinity for ICAM-1 than the parental mouse scFv (Table 4).

TABLE 4

Mouse 1A6 scFv and Humanized 1A6 scFv

| ScFv | $K_D$ (M) | EC 50 (µM)* |
|---|---|---|
| Msc1A6 | $1.18 \times 10^{-6}$ | >10 |
| HscA | $1.50 \times 10^{-7}$ | 2.8 |
| HscB | $2.62 \times 10^{-8}$ | 0.19 |
| HscC | $5.80 \times 10^{-8}$ | 0.22 |
| HscD | $2.33 \times 10^{-8}$ | 0.05 |
| HscF | $4.60 \times 10^{-8}$ | 0.29 |
| HscH | $2.09 \times 10^{-8}$ | 4.2 |
| HscI | $1.50 \times 10^{-7}$ | >10 |

*50% protection of HeLa cells against HRV15 infection at 1 MOI.

Example 5

This example describes data demonstrating that humanized 1 A6 antibodies protect against HRV infection. This example also describes data that demonstrate that protection was significantly greater than mouse 1A6 antibody.

HeLa cells were plated at $1 \times 10^5$ cells per well of a 48-well tissue culture dish and cultured for 24 hours. Culture medium was aspirated and 100 µl of humanized 1 A6 proteins was added to each well at the dilution indicated. The plates were incubated for one hour in a 37° C. incubator, the protein solution removed, 200 µl HRV15 (at MOI of 1) was added and the plates incubated for one hour at 33° C. The cells were then washed and 1 ml/well growth medium added. The infected cells were incubated at 33° C. for 48 hours. The medium was then aspirated and the remaining viable cells stained with crystal violet. Finally, the crystal violet was extracted with 2 ml methanol per well, and the extracted stain determined by measuring the $A_{570}$. The percentage protection was calculated for each point in triplicate using the formula:

$$(100)\% \text{ protection} = \frac{\text{(Absorbance of sample} - \text{Absorbance of virus only)}}{\text{(Absorbance of uninfected cells} - \text{Absorbance of virus only)}}$$

The protection efficacy was quantified as $EC_{50}$, which is the dose of an antibody protein which can protect 50% of hela cells from HRV infection. $EC_{50}$, of several humanized 1A6 proteins are summarized in Table 2, and the data from this protection assay is shown in FIG. 4. This assay revealed that the EC50 of Hum19 scFv protein was more than sixty times higher than that of the parental mouse 1A6 scFv protein (FIG. 4). In vitro protection results correlate well with the antibody binding affinity.

The invention claimed is:

1. An antibody that binds ICAM-1 comprising:
   (i) a $V_H$ region of SEQ ID NO:9, and a $V_L$ region of SEQ ID NO:11;
   (ii) a $V_H$ region of SEQ ID NO:9, and a variant $V_L$ region of SEQ ID NO:11;
   (iii) a variant $V_H$ region of SEQ ID NO:9, and a $V_L$ region of SEQ ID NO:11; or
   (iv) a variant $V_H$ region of SEQ ID NO:9, and a variant $V_L$ region of SEQ ID NO:11;
   wherein the variant $V_H$ region comprises one or more amino acid substitutions at positions 37, 61, 62, 63, 64, 65, 70, 72, 74, and 98 of SEQ ID NO:9; and wherein the variant $V_L$ region comprises an amino acid substitution at position 49 of SEQ ID NO:11.

2. The antibody of claim 1 having a protective efficacy against pathogen infection greater than an antibody having mouse monoclonal antibody 1A6 variable domains.

3. The antibody of claim 1 having a binding affinity for ICAM-1 greater than an antibody having mouse monoclonal antibody 1A6 variable domains.

4. The antibody of claim 2, wherein said pathogen is human rhinovirus (HRV), coxsackie A virus, respiratory syncytial virus or malaria.

5. The antibody of claim 1, wherein said antibody comprises a multimerization domain.

6. The antibody of claim 5, wherein said antibody comprises a linker between said antibody and said multimerization domain.

7. The antibody of claim 6, further comprising one or more identical or different antibodies that form a multimer.

8. The antibody of claim 7, wherein said multimer is a homodimer, heterodimer, trimer, tetramer or pentamer.

9. The antibody of claim 1, said antibody having a protective efficacy at least two times greater than mouse monoclonal antibody 1A6.

10. The antibody of claim 1, wherein said antibody is an intact immunoglobulin molecule comprising two full-length heavy chains and two full-length light chains.

11. A nucleic acid sequence encoding the antibody of claim 1.

12. A vector comprising the nucleic acid sequence of claim 11.

13. A pharmaceutical composition comprising the antibody of claim 1 and a pharmaceutically acceptable carrier.

14. A method for inhibiting pathogen infection of a cell, said method comprising contacting a pathogen or cell susceptible to the pathogen infection with the antibody of claim 1 in an amount sufficient to inhibit pathogen infection of the cell.

15. The method of claim 14, wherein said cell is an epithelial cell.

16. The antibody of claim 1, wherein the variant $V_H$ region comprises one or more amino acid substitutions selected from the group consisting of (i) said position 37 is Met; (ii) said position 61 is Asp; (iii) said position 62 is Pro; (iv) said position 63 is Lys; (v) said position 65 is Gln; (vi) said position 70 is Met; (vii) said position 72 is Arg, Ser or Ala; (viii) said position 74 is Thr; (ix) said position 98 is Arg, Ala or Asp; and (x) any combination thereof.

17. The antibody of claim 1, comprising the $V_H$ region of SEQ ID NO:9, and the $V_L$ region of SEQ ID NO:11.

18. The antibody of claim 1, comprising the $V_H$ region of SEQ ID NO:9 and the variant $V_L$ region of SEQ ID NO:11.

19. The antibody of claim 1, comprising the variant $V_H$ region of SEQ ID NO:9 and the $V_L$ region of SEQ ID NO:11.

20. The antibody of claim 1, comprising the variant $V_H$ region of SEQ ID NO:9 and the variant $V_L$ region of SEQ ID NO:11.

21. The antibody of claim 1, wherein the variant $V_L$ region comprises the following amino acid substitution: said position 49 is a Lys.

22. The antibody of claim 16, wherein the variant $V_L$ region comprises the following amino acid substitution: said position 49 is a Lys.

23. The antibody of claim 18, wherein the variant $V_L$ region comprises the following amino acid substitution: said position 49 is a Lys.

24. The antibody of claim 20, wherein the variant $V_L$ region comprises the following amino acid substitution: said position 49 is a Lys.

25. The antibody of claim 19, wherein the variant $V_H$ region comprises one or more amino acid substitutions selected from the group consisting of (i) said position 37 is Met; (ii) said position 61 is Asp; (iii) said position 62 is Pro; (iv) said position 63 is Lys; (v) said position 65 is Gln; (vi) said position 70 is Met; (vii) said position 72 is Arg, Ser or Ala; (viii) said position 74 is Thr; (ix) said position 98 is Arg, Ala or Asp; and (x) any combination thereof.

26. The antibody of claim 25, wherein the variant $V_H$ region comprises the following amino acid substitutions: said position 72 is Ser, and said position 98 is Asp.

27. The antibody of claim 25, wherein the variant $V_H$ region comprises the following amino acid substitution: said position 72 is Ser.

28. The antibody of claim 25, wherein the variant $V_H$ region comprises the following amino acid substitutions: said position 61 is Asp, said position 62 is Pro, said position 63 is Lys, said position 65 is Gln, and said position 72 is Ala.

29. The antibody of claim 25, wherein the variant $V_H$ region comprises the following amino acid substitution: said position 72 is Ala.

30. The antibody of claim 25, wherein the variant $V_H$ region comprises the following amino acid substitutions: said position 61 is Asp, said position 62 is Pro, said position 63 is Lys, said position 65 is Gln, and said position 72 is Ala.

31. The antibody of claim 25, wherein the variant $V_H$ region comprises the following amino acid substitutions: said position 37 is Met, said position 61 is Asp, said position 62 is Pro, said position 63 is Lys, said position 65 is Gln, said position 70 is Met, said position 72 is Ala, and said position 74 is Thr.

32. The antibody of claim 20, wherein the variant $V_H$ region comprises one or more amino acid substitutions selected from the group consisting of (i) said position 37 is Met; (ii) said position 61 is Asp; (iii) said position 62 is Pro; (iv) said position 63 is Lys; (v) said position 65 is Gln; (vi) said position 70 is Met; (vii) said position 72 is Arg, Ser or Ala; (viii) said position 74 is Thr; (ix) said position 98 is Arg, Ala or Asp; and (x) any combination thereof.

33. The antibody of claim 32, wherein the variant $V_L$ region comprises the following amino acid substitution: said position 49 is a Lys.

34. The antibody of claim 32, wherein the variant $V_H$ region comprises the following amino acid substitutions: said position 72 is Ser, and said position 98 is Ala.

35. The antibody of claim 34, wherein the variant $V_L$ region comprises the following amino acid substitution: said position 49 is a Lys.

36. The antibody of claim 32, wherein the variant $V_H$ region comprises the following amino acid substitution: said position 72 is Ser.

37. The antibody of claim 36, wherein the variant $V_L$ region comprises the following amino acid substitution: said position 49 is a Lys.

38. The antibody of claim 32, wherein the variant $V_H$ region comprises the following amino acid substitutions: said position 61 is Asp, said position 62 is Pro, said position 63 is Lys, said position 65 is Gln, and said position 72 is Ala.

39. The antibody of claim 38, wherein the variant $V_L$ region comprises the following amino acid substitution: said position 49 is a Lys.

40. The antibody of claim 32, wherein the variant $V_H$ region comprises the following amino acid substitution: said position 72 is Ala.

41. The antibody of claim 40, wherein the variant $V_L$ region comprises the following amino acid substitution: said position 49 is a Lys.

42. The antibody of claim 32, wherein the variant $V_H$ region comprises the following amino acid substitutions: said position 61 is Asp, said position 62 is Pro, said position 63 is Lys, said position 65 is Gln, and said position 72 is Ala.

43. The antibody of claim 42, wherein the variant $V_L$ region comprises the following amino acid substitution: said position 49 is a Lys.

44. The antibody of claim 32, wherein the variant $V_H$ region comprises the following amino acid substitutions: said position 37 is Met, said position 61 is Asp, said position 62 is Pro, said position 63 is Lys, said position 65 is Gln, said position 70 is Met, said position 72 is Ala, and said position 74 is Thr.

45. The antibody of claim 44, wherein the variant $V_L$ region comprises the following amino acid substitution: said position 49 is a Lys.

46. A method for inhibiting pathogen infection of a cell, said method comprising contacting a pathogen or cell susceptible to the pathogen infection with the antibody of claim 17 in an amount sufficient to inhibit pathogen infection of the cell.

47. A method for inhibiting pathogen infection of a cell, said method comprising contacting a pathogen or cell susceptible to the pathogen infection with the antibody of claim 26 in an amount sufficient to inhibit pathogen infection of the cell.

48. A method for inhibiting pathogen infection of a cell, said method comprising contacting a pathogen or cell susceptible to the pathogen infection with the antibody of claim 27 in an amount sufficient to inhibit pathogen infection of the cell.

49. A method for inhibiting pathogen infection of a cell, said method comprising contacting a pathogen or cell susceptible to the pathogen infection with the antibody of claim 28 in an amount sufficient to inhibit pathogen infection of the cell.

50. A method for inhibiting pathogen infection of a cell, said method comprising contacting a pathogen or cell susceptible to the pathogen infection with the antibody of claim 29 in an amount sufficient to inhibit pathogen infection of the cell.

51. A method for inhibiting pathogen infection of a cell, said method comprising contacting a pathogen or cell susceptible to the pathogen infection with the antibody of claim 41 in an amount sufficient to inhibit pathogen infection of the cell.

52. A method for inhibiting pathogen infection of a cell, said method comprising contacting a pathogen or cell susceptible to the pathogen infection with the antibody of claim 43 in an amount sufficient to inhibit pathogen infection of the cell.

53. A method for inhibiting pathogen infection of a cell, said method comprising contacting a pathogen or cell susceptible to the pathogen infection with the antibody of claim 45 in an amount sufficient to inhibit pathogen infection of the cell.

\* \* \* \* \*